(12) United States Patent
Takato

(10) Patent No.: US 9,341,838 B2
(45) Date of Patent: May 17, 2016

(54) OBJECTIVE OPTICAL SYSTEM

(71) Applicant: OLYMPUS CORPORATION, Tokyo (JP)

(72) Inventor: Hideyasu Takato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/531,434

(22) Filed: Nov. 3, 2014

(65) Prior Publication Data

US 2015/0103418 A1    Apr. 16, 2015

Related U.S. Application Data

(63) Continuation of application No. PCT/JP2013/081023, filed on Nov. 18, 2013.

(30) Foreign Application Priority Data

Feb. 28, 2013   (JP) .................................. 2013-039288

(51) Int. Cl.
| | |
|---|---|
| *G02B 9/00* | (2006.01) |
| *G02B 23/24* | (2006.01) |
| *G02B 15/173* | (2006.01) |
| *G02B 9/62* | (2006.01) |
| *A61B 1/00* | (2006.01) |

(52) U.S. Cl.
   CPC ................ *G02B 23/243* (2013.01); *G02B 9/62* (2013.01); *G02B 15/173* (2013.01); *G02B 23/2438* (2013.01); *A61B 1/00188* (2013.01)

(58) Field of Classification Search
   CPC ................................ G02B 13/24; G02B 13/00
   USPC .................................................. 359/708, 754
   See application file for complete search history.

(56) References Cited

U.S. PATENT DOCUMENTS

| | | | |
|---|---|---|---|
| 4,312,572 A | 1/1982 | Yamashita et al. | |
| 6,252,723 B1 | 6/2001 | Nagaoka | |
| 6,433,937 B1 | 8/2002 | Konno | |
| 7,499,226 B2 * | 3/2009 | Takato | 359/690 |
| 7,982,975 B2 * | 7/2011 | Takato | 359/754 |
| 2007/0206293 A1 | 9/2007 | Takato | |
| 2009/0002845 A1 | 1/2009 | Hosoya et al. | |

(Continued)

FOREIGN PATENT DOCUMENTS

| | | |
|---|---|---|
| JP | 61-44283 | 10/1986 |
| JP | 4-218012 | 8/1992 |

(Continued)

OTHER PUBLICATIONS

International Search Report, dated Feb. 18, 2014, issued in corresponding International Application No. PCT/JP2013/081023.

*Primary Examiner* — James Greece
(74) *Attorney, Agent, or Firm* — Kenyon & Kenyon LLP

(57) ABSTRACT

An objective optical system consists of, from an object side to an image side: a first lens group having positive optical power; a second lens group having negative optical power; and a third lens group having positive optical power, wherein the first lens group includes, from the object side to the image side, a first lens having negative optical power and a second lens having positive optical power, and the second lens group is moved according to a change in an object distance to perform focusing, and the following conditional expressions are satisfied:

$$-19 < f2/f1 < -3.5$$

$$0.5 < v/f < 1.1$$

where f2 is a focal length of the second lens, f1 is a focal length of the first lens, v is an amount of movement of the second lens group, and f is a focal length of an entire system during the most distant view observation.

2 Claims, 21 Drawing Sheets

(56) References Cited

U.S. PATENT DOCUMENTS

| | | | |
|---|---|---|---|
| 2009/0231725 A1 | 9/2009 | Matsunaga et al. |
| 2010/0033834 A1 | 2/2010 | Matsusaka et al. |
| 2011/0235192 A1 | 9/2011 | Uzawa et al. |
| 2011/0273611 A1 | 11/2011 | Matsusaka et al. |
| 2012/0194924 A1 | 8/2012 | Sakai et al. |
| 2012/0257100 A1 | 10/2012 | Imaoka et al. |
| 2013/0033768 A1 | 2/2013 | Sunaga et al. |

FOREIGN PATENT DOCUMENTS

| | | |
|---|---|---|
| JP | 10-20194 | 1/1998 |
| JP | 11-316339 | 11/1999 |
| JP | 2000-267002 | 9/2000 |
| JP | 2012-226309 | 11/2002 |
| JP | 3349766 | 11/2002 |
| JP | 2007-233036 | 9/2007 |
| JP | 2008-070411 | 3/2008 |
| JP | 2009-222891 | 10/2009 |
| JP | 2009-251432 | 10/2009 |
| JP | 4659645 | 1/2011 |
| JP | 2012-32576 | 2/2012 |
| JP | 2012-159613 | 8/2012 |
| JP | 2013-37080 | 2/2013 |
| WO | 2008/072466 | 6/2008 |
| WO | 2010/137238 | 12/2010 |
| WO | 2011/027690 | 3/2011 |

* cited by examiner

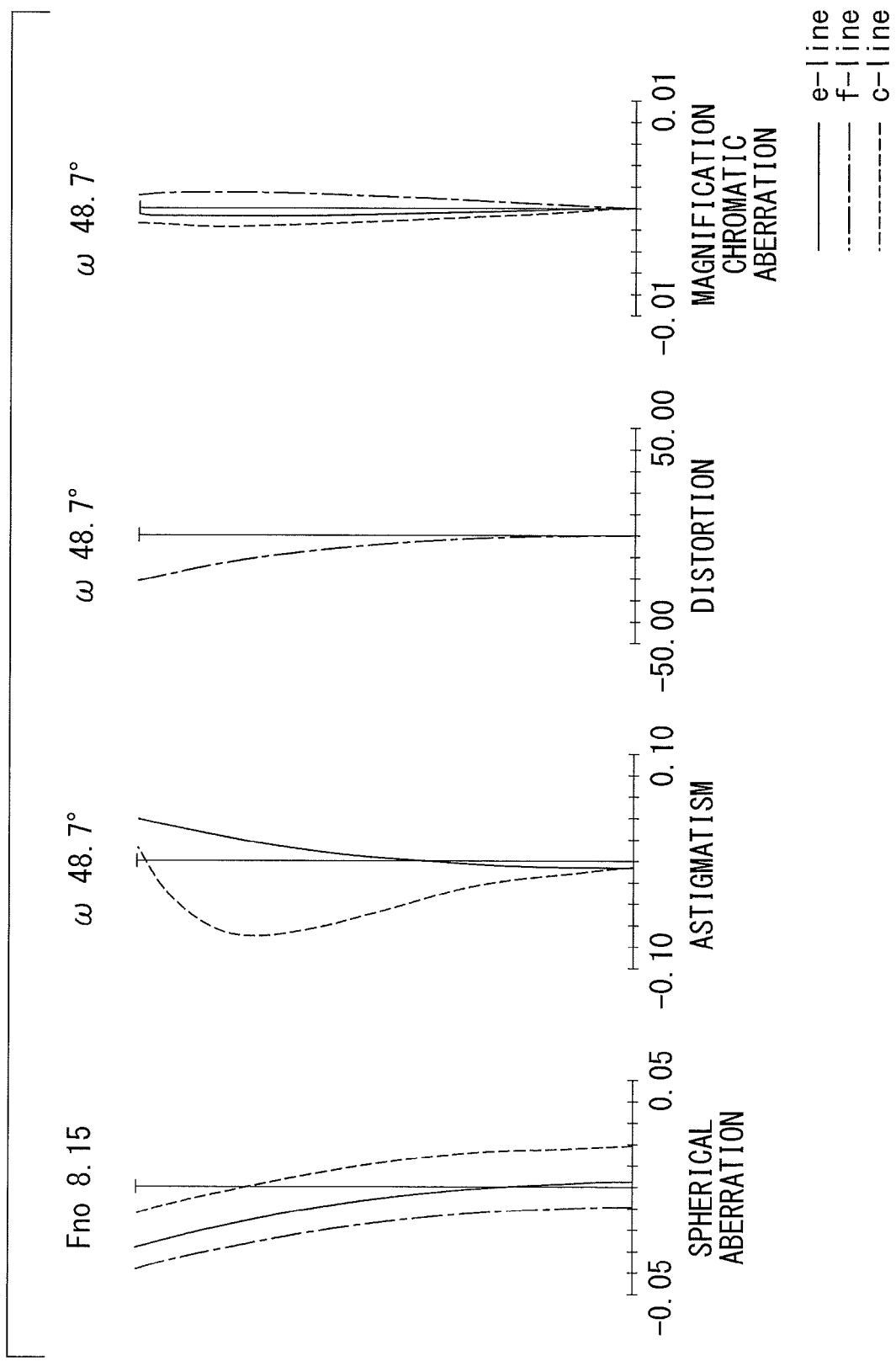

OBJECTIVE OPTICAL SYSTEM

CROSS-REFERENCE TO RELATED APPLICATIONS

This is a continuation of International Application PCT/JP2013/081023, with an international filing date of Nov. 18, 2013, which is hereby incorporated by reference herein in its entirety. This application claims the benefit of Japanese Patent Application No. 2013-039288, the content of which is incorporated herein by reference.

TECHNICAL FIELD

The present invention relates to optical systems having a focusing function and relates, for example, to endoscope objective lenses that enable magnified observation and photographic lenses of digital cameras or video cameras that are capable of macro-photography, portable cameras, and so forth.

BACKGROUND ART

Recently, in the field of medical endoscopes, there has been a growing need for optical systems that enable magnified observation in order to perform qualitative diagnosis of lesions.

As an example of such endoscope objective lenses, Patent Literature 1 to Patent Literature 5 disclose lenses that enable magnified observation, having a positive-negative-positive three-group structure in which the second group moves to perform focusing. In addition, Patent Literature 6 discloses lenses having a negative-positive-negative three-group structure in which the second group moves to perform focusing.

In accordance with the need for high-quality diagnostic images, the precision of image-capturing devices such as CCDs and CMOS devices is becoming higher and higher, and with regard to optical systems, there is a demand for not only focusing functions, but also to make them compatible with the increasingly higher precision of image-capturing devices.

Endoscope observation requires a large observation depth from near points to far points, and therefore, optical systems that are almost panfocal, with a large Fno and stopped-down aperture, are required.

On the other hand, the Fno of the optical systems must fall within the following range in order to avoid the effects of diffraction.

$$Fno < 2 \times P/1.22/\lambda$$

As image-capturing devices gain higher and higher pixel counts, they are influenced by diffraction, and since the Fno cannot be made very large, the depth becomes small.

CITATION LIST

Patent Literature

{PTL 1}
Japanese Examined Patent Application, Publication No. SHO 61-44283
{PTL 2}
The Publication of Japanese Patent No. 3349766
{PTL 3}
Japanese Unexamined Patent Application, Publication No. HEI 11-316339
{PTL 4}
The Publication of Japanese Patent No. 4659645
{PTL 5}
Japanese Unexamined Patent Application, Publication No. 2012-32576
{PTL 6}
Japanese Unexamined Patent Application, Publication No. 2000-267002

SUMMARY OF INVENTION

In light of these circumstances, in a magnifying endoscope, because the distance between the objective lens and the object is small, particularly during magnified observation, and the observation depth is thus small, the Fno of the optical system is stopped down to the diffraction limit. At this time, in a conventional magnifying endoscope, a sufficient depth is achieved, and there is no problem in practice with the Fno during normal observation; however, with an objective lens that is compatible with high-pixel-count image-capturing devices, the observation depth is small, and it is difficult to ensure an adequate observation range. Therefore, it is not possible to focus on a lesion to be examined.

In addition, when it is desired to ensure an adequate observation depth, the object should be observed at a somewhat long distance, and in the case of a long distance, the amount of movement of the focusing lens becomes small. However, when the amount of movement of the lens is small, the sensitivity to changes in the magnification factor is higher, and therefore, the usability is poor when performing manual focusing to a position that the doctor wishes to examine. Therefore, from the viewpoint of ensuring a magnification factor of a certain level, it is undesirable to make the object distance during magnified observation a somewhat long distance.

The optical system described in the above-described Patent Literature 1 has a high magnification factor but a small viewing field during normal observation; therefore, the task of identifying a lesion from a wide observation viewing field is difficult.

The optical systems described in Patent Literature 2 to Patent Literature 4 have sufficiently high magnification factor, but the depth range during close-up observation is small; therefore, focusing is difficult, and the lesion easily goes out of focus due to pulsation etc. Therefore, it is necessary to perform focusing fine adjustment during magnified observation; however, since the focal region is a pinpoint, it is difficult to obtain information about the area around the lesion. In addition, when it is desired to capture a still picture, out-of-focus images tend to be captured.

With the optical system described in Patent Literature 5, in the negative-positive-negative three-group structure, because the only positive group is the second group, which is a movable group, there is a tendency for the power of this second group to be high. Therefore, aberration variations at the time of normal observation and magnified observation are high, making this optical system unsuitable as the objective lens for high-precision image-capturing devices, for which a higher-performance optical system is required. In particular, the variation in chromatic aberration is large, causing color bleeding in the image observed on the monitor.

The optical system described in Patent Literature 6 is compatible with high-pixel-count image-capturing devices but the viewing angle in normal observation is about 130°, and therefore, it cannot be said to offer a sufficiently wide angle.

Thus, when the optical systems disclosed in each of the above-described Patent Literatures are made compatible with high-precision, high-pixel-count image-capturing devices, even if the Fno during magnification is stopped down to the diffraction limit, the Fno during normal observation becomes too small, and therefore, the desired depth cannot be obtained.

The present invention provides a high-performance objective optical system that can ensure an adequate depth from normal observation to magnified observation, that has a wide viewing angle, and that can be easily focused on a lesion.

One aspect of the present invention is an objective optical system including, in order from an object side to an image side: a first lens group having positive optical power; a second lens group having negative optical power; and a third lens group having positive optical power, wherein the first lens group includes, in order from the object side to the image side, a first lens having negative optical power and a second lens having positive optical power, and the second lens group is moved according to a change in an object distance to perform focusing, and conditional expressions (1) and (2) below are satisfied:

$$-19 < f2/f1 < -3.5 \qquad (1)$$

$$0.5 < v/f < 1.1 \qquad (2)$$

Here, f2 is a focal length of the second lens, and f1 is a focal length of the first lens.

In addition, v is an amount of movement of the second lens group, and f is a focal length of an entire system during the most distant view observation (normal observation).

BRIEF DESCRIPTION OF DRAWINGS

FIG. 5 shows aberration diagrams of the objective optical system in FIG. 2C in the magnified observation state.

DESCRIPTION OF EMBODIMENT

An objective optical system according to an embodiment of the present invention will be described below with reference to the drawings.

Figure 1:
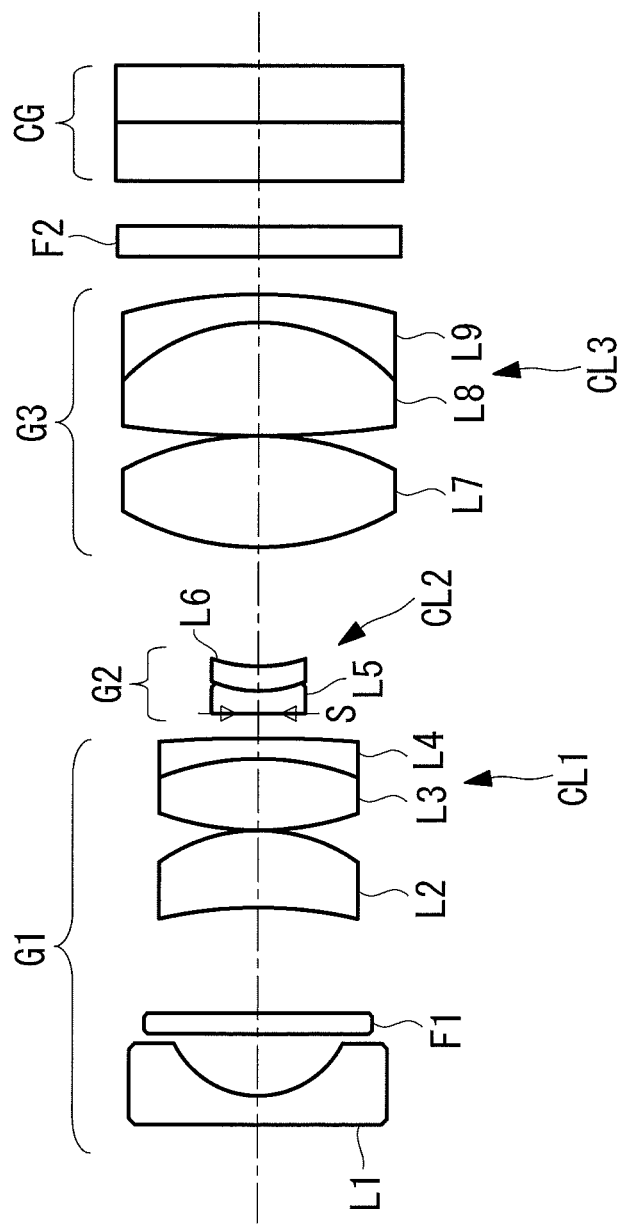
FIG. 1 is a cross-sectional view showing the overall configuration of an objective optical system according to an embodiment of the present invention.

FIG. 1 is a cross-sectional view showing the overall configuration of an objective optical system according to this embodiment. As shown in FIG. 1, the objective optical system includes, in order from the object side, a first lens group G1 having positive optical power (hereinafter referred to simply as "positive"), an aperture stop S, a second lens group G2 having negative optical power (hereinafter referred to simply as "negative"), and a third lens group G3 having positive optical power.

The positive first lens group G1 includes, in order from the object side, a negative first lens L1, a first parallel flat plate F1, a positive second lens L2, a positive third lens L3, and a negative fourth lens L4. Of these components, the positive third lens L3 and the negative fourth lens L4 are combined to form a combined lens CL1.

The negative second lens group G2 includes, in order from the object side, a combined lens CL2 in which a negative fifth lens L5 and a positive sixth lens L6 are combined and moves along the optical axis together with an aperture stop S, which is disposed between the first lens group G1 and the second lens group G2.

The positive third lens group G3 includes, in order from the object side, a positive seventh lens L7 and a combined lens CL3 in which a positive eighth lens L8 and a negative ninth lens L9 are combined.

Then, an image-capturing device, which is not illustrated, is disposed close to the image plane of the objective optical system, constituting an image-capturing optical system together with the objective optical system. A parallel flat plate F2 and a cover glass CG are bonded to the image-capturing device to protect the imaging surface.

The objective optical system is configured so as to satisfy the following conditional expressions.

$$-19 < f2/f1 < -3.5 \quad (1)$$

$$0.5 < v/f < 1.1 \quad (2)$$

where f2 is a focal length of the second lens, and f1 is a focal length of the first lens.

Also, v is an amount of movement of the second lens group, and f is a focal length of an entire system during the most distant view observation (normal observation).

Conditional expression (1) is intended to ensure sufficient depth by setting an appropriate focal length of the entire system, contributing to a more compact and higher performance lens system.

Therefore, when the lower limit of conditional expression (1) is exceeded, the focal length of the second lens group becomes large, thus making the focal length of the entire system large, and therefore, the depth is small from the most distant view observation (normal observation) to magnified observation, and it becomes particularly difficult to ensure the required depth during magnified observation.

In addition, when the upper limit of conditional expression (1) is exceeded, the focal length of the second lens group becomes small relative to the focal length of the first lens group, and although this is beneficial in terms of making the overall lens system more compact, the variation in chromatic aberrations becomes large. In particular, the amount of magnification chromatic aberration that is generated becomes large, which causes color bleeding.

Conditional expression (2) involves the amount of movement of the second group from normal observation to magnified observation.

Thus, when the lower limit of conditional expression (2) is exceeded, the amount of movement of the second lens group, which is the focusing group, is small, and the sensitivity at this time becomes too high, making it impossible to perform focusing well.

In addition, when the upper limit of conditional expression (2) is exceeded, the amount of movement of the second lens group 2 is large, thus focusing on a closer object point. In other words, this means that the observation distance is small.

When the observation distance is small, the observation magnification factor becomes large, making it easy to see minute lesions; however, since the depth is small, focusing is difficult, resulting in poor usability. Furthermore, the stroke of a lens driving part becomes long, increasing the overall length of the lens system and resulting in a bulky system. In addition, in cases where an actuator is built in for driving the lens, etc., this inevitably causes the actuator part to become large due to the long stroke.

In an endoscope optical system 1 according to this embodiment, the magnification factor is made no larger than is necessary to ensure an adequate depth during magnified observation. Thus, when observing the fine structure of a lesion, capillaries, etc. in detail, a high-resolution image-capturing device and a high-performance optical system that is compatible therewith are preferable.

Hence, it is more preferable to optimize the power of each lens group using the following conditional expressions.

That is, the objective optical system is preferably configured so as to satisfy conditional expressions (3) to (13) below.

$$0.95 < g1/f < 1.65 \quad (3)$$

$$-4 < g2/f < -2 \quad (4)$$

$$2.1 < g3/f < 2.9 \quad (5)$$

$$0.7 < |g2/g3| < 1.5 \quad (6)$$

$$0.3 < |g1/g2| < 0.5 \quad (7)$$

Here, g1 is a focal length of the first lens group, g2 is a focal length of the second lens group, and g3 is a focal length of the third lens group.

Conditional expressions (3) to (5) are conditional expression required for realizing a high-resolution objective optical system.

When the lower limit of conditional expression (3) is exceeded, the amount of spherical aberration generated becomes particularly large during magnified observation. Also, field curvature during normal observation is inclined to the under side, which is undesirable. In addition, when the upper limit of conditional expression (3) is exceeded, the image plane during magnified observation is strongly curved to the under side near the center of the screen, and is strongly curved to the over side at the edges of the screen.

When the lower limit of conditional expression (4) is exceeded, the axial chromatic aberration and the magnification chromatic aberration both become large. When the upper limit of conditional expression (4) is exceeded, the image plane becomes inclined towards the under side, and the drop in resolving power is considerable.

Conditional expression (5) is a conditional expression for suppressing movement of the image plane in the normal observation state and the magnified observation state; when the range of the conditional expression is exceeded, image plane movement at the extreme edges of the screen is large. That is to say, when the lower limit of conditional expression (5) is exceeded, the image plane goes to the under side during normal observation and goes to the over side during magnified observation. In addition, when the upper limit of conditional expression (5) is exceeded, the image plane goes to the over side during normal observation and goes to the under side during magnified observation.

Conditional expressions (6) and (7) are, like conditional expressions (3) to (5), conditional expressions that are necessary for realizing a high-resolution objective optical system and also contribute to realizing a compact optical system.

In an optical system that is compatible with a high-pixel-count image-capturing device, correction of chromatic aberrations is important; however, conditional expression (6), together with conditional expression (4), is related mainly to correction of magnification chromatic aberrations.

When the lower limit of conditional expression (6) is exceeded, the magnification chromatic aberration at the f-line becomes large on the over side, and during magnified observation, the magnification chromatic aberration at the c-line is also large on the under side. In addition, since the focal length of the third lens group is large, the back focal length of the lens system and the overall length of the lens become large, resulting in a bulky system. A large overall length of the lens system means, in other words, that the rigid length at the tip of the endoscope becomes large, and therefore, the burden on the patient at the time of insertion is also large, which is undesirable.

When the upper limit of conditional expression (6) is exceeded, particularly during normal observation, the c-line becomes large on the over side, and the magnification chromatic aberration at the f-line becomes large on the under side.

Conditional expression (7) is related to correction of spherical aberration, comatic aberration, and axial chromatic aberration.

When the lower limit of conditional expression (7) is exceeded, spherical aberration is undercorrected. In particular, during close-up magnification, where the magnification factor is large, when the amount of spherical aberration generated is large, not only it is impossible to obtain a high-resolution image, regardless of the fact that a magnified image is obtained, but this could also cause coma flare.

When the upper limit of conditional expression (7) is exceeded, the axial chromatic aberration at the f-line, and also at the g-line, from normal observation to magnified observation is large. In addition, the variation of chromatic aberration is large. In particular, since the amount of magnification chromatic aberration generated is large, this also causes color bleeding. Furthermore, the overall lens system inevitably becomes bulky due to the large focal length of the first lens group.

Conditional expressions (8) and (9) are defined as shown below and are related to the viewing angle.

$$w1 > 75 \qquad (8)$$

$$w2 < 55 \qquad (9)$$

Here, w1 is a half viewing angle during normal observation, and w2 is a half viewing angle during magnified observation.

Conditional expression (8) is a conditional expression involving the half viewing angle during normal observation. For example, to reduce the risk of overlooking a lesion in a fold when examining the large intestine, there is a strong desire for an endoscope optical system with a wide angle, and w1 preferably takes a range in conditional expression (8).

Conditional expression (9) is a conditional expression involving the half viewing angle during magnified observation. A non-uniform intensity distribution of the illumination tends to occur during magnified observation because observation is conducted close to the subject, and therefore, a narrow-angle optical system is preferred, and w2 preferably takes a range in conditional expression (9).

Conditional expression (10), which is defined as follows, is a conditional expression related to the compactness and the magnification factor of the optical system.

$$1.0 < ltl/f \cdot (\beta 2/\beta 1) < 1.8 \qquad (10)$$

Here, ltl is a total length of the optical system (a distance from a object-side surface of the first lens to the imaging surface), β1 is a magnification factor at the best object distance in the normal observation state, and β2 is a magnification factor at the best object distance in the magnified observation state.

By satisfying conditional expression (10), it becomes unnecessary to increase the overall length of the optical system, and it is possible to realize a compact optical system while achieving a sufficient change in the magnification factor.

In addition, when the upper limit of conditional expression (10) is exceeded, the change in the magnification factor between normal observation and magnified observation is small, and therefore, the magnification factor during close-up observation when using the endoscope as a magnifying endoscope is unsatisfactory.

A high-pixel-count image-capturing device preferably satisfies conditional expression (11) below.

$$0.4 < IH/p/1000 < 0.7 \qquad (11)$$

Here, IH is the maximum image height, and p is the pixel pitch.

When the lower limit of conditional expression (11) is exceeded, the pitch of the image-capturing device becomes large, and it is thus difficult to call it a high-pixel-count image-capturing device. When the upper limit of conditional expression (11) is exceeded, although the image-capturing device has a higher pixel count, it tends to be affected by diffraction, and the required depth of field of the subject cannot be obtained.

Furthermore, the maximum ray height at the rear surface of the final lens preferably satisfies conditional expression (12) below.

$$0.5 < h2/h1 < 1.2 \qquad (12)$$

Here, h2 is the maximum ray height at the final surface during magnified observation, and h1 is the maximum ray height at the final surface during normal observation.

In the case where conditional expression (12) is not satisfied, the angle of incidence on the image-capturing device does not fall within a prescribed range, causing a reduction in light intensity at the edges.

In particular, when the lower limit of conditional expression (12) is exceeded, there is a remarkable reduction in light intensity at the edges during magnified observation, which is undesirable. When the upper limit of conditional expression (12) is exceeded, the ray height at the third group during normal observation is high, and the lens diameter ends up being large. When the tip diameter of the endoscope increases due to the large lens diameter, a smooth operation at the time of insertion becomes difficult, which increases the burden on the patient.

To reduce the lens diameter, the upper limit of conditional expression (12) is more preferably restricted as follows.

$$0.5 < h2/h2 < 0.85 \qquad (12)'$$

To reduce the lens diameter of the first lens group, it is preferable to satisfy conditional expression (13) below.

$$0.5 < Enp/f < 1.5 \qquad (13)$$

Here, Enp is the entrance pupil position during normal observation.

When the lower limit of conditional expression (13) is exceeded, the focal length of the entire system becomes large relative to the entrance pupil position, high distortion occurs in order to ensure an adequate viewing angle, and the difference in magnification factors between the center and edges of the screen is large, which is undesirable.

When the upper limit of conditional expression (13) is exceeded, the diameter of the first lens becomes large, thus causing the objective optical system to become bulky.

To reduce the size of the objective lens even further, the upper limit of conditional expression (13) is preferably restricted as follows.

$$0.5 < Enp/f < 1.0 \qquad (13)'$$

The objective optical system according to this embodiment configured as described above includes, in order from the object side to the image side, the positive first lens group G1, the negative second lens group G2, and the positive third lens group G3, where the first lens group G1 includes, in order from the object side to the image side, the negative first lens L1 and the positive second lens L2, and during focusing, the second lens group G2 is moved according to changes in the object distance, and the objective optical system is configured so as to satisfy conditional expression (1) and conditional expression (2) above. By doing so, it is possible to specify the lens group to be moved during magnified observation and to restrict the amount of movement thereof, which makes it possible to maintain an appropriate focal length of the entire system. Therefore, it is possible to ensure the desired depth, and also to reduce the size and increase the performance of the lens system.

The second lens L2 is preferably a positive meniscus lens in which the surface at the object side is a concave surface; by doing so, the front focal position is located at the image plane side, and therefore, the magnification factor does not become larger than required even when observing a short-range object point, and it is possible to expand the depth.

EXAMPLES

The objective optical system according to the above embodiment affords the advantages that it is possible to ensure an adequate depth from normal observation to magnified observation, to provide a wide viewing angle, and to easily perform focusing on a lesion.

Next, Examples 1 to 5 of the objective optical system according to the above-described embodiment will be described with reference to FIGS. 2 to 21. In the lens data shown in each of the Examples, r indicates a radius of curvature (unit: mm), d indicates an inter-surface spacing (mm), Ne indicates a refractive index at the e-line, and Vd indicates the Abbe number at the d-line.

Example 1

Figure 2A:
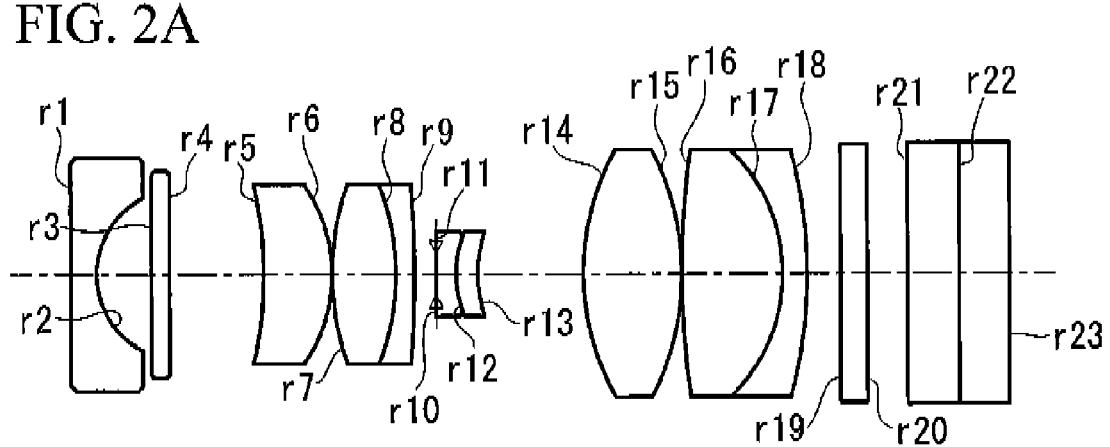
FIG. 2A is a cross-sectional view showing the overall configuration of an objective optical system according to Example 1 of the present invention, and shows a normal observation state.
Figure 2B:
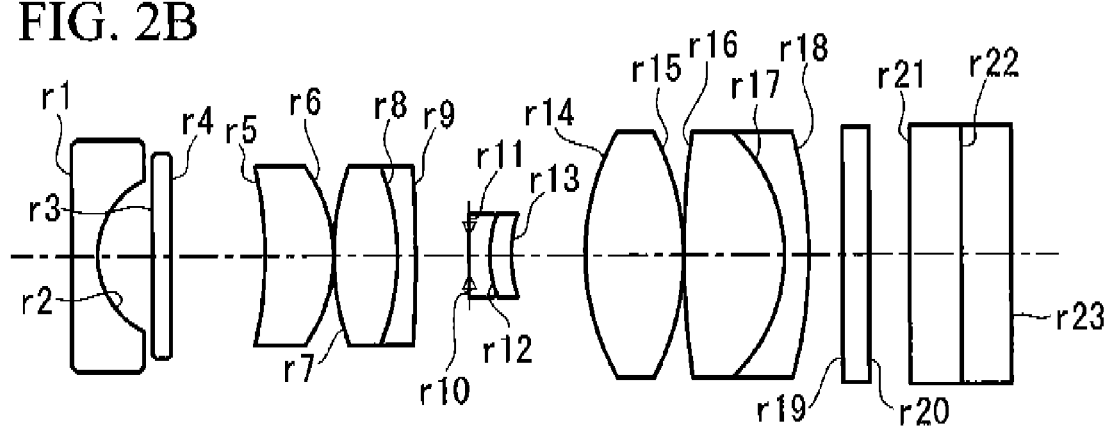
FIG. 2B is a cross-sectional view showing the overall configuration of an objective optical system according to Example 1 of the present invention, and shows an intermediate state.
Figure 2C:
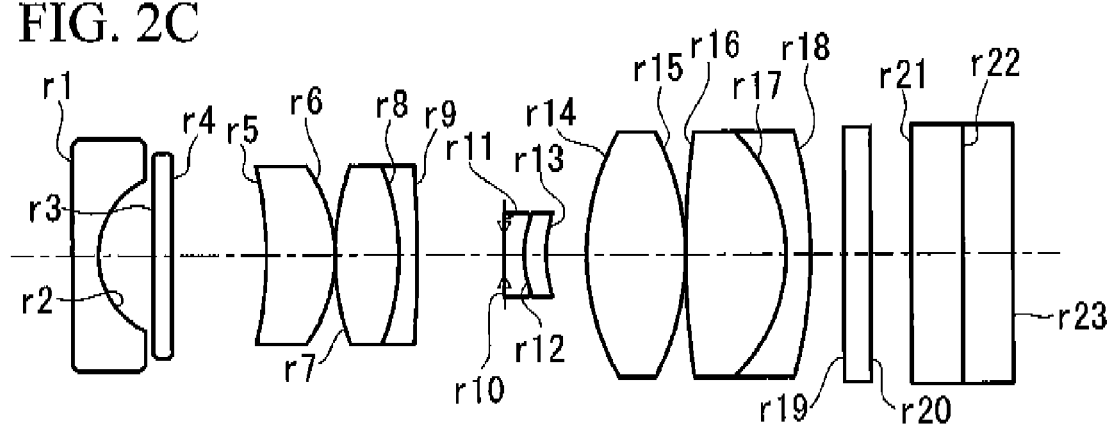
FIG. 2C is a cross-sectional view showing the overall configuration of an objective optical system according to Example 1 of the present invention, and shows a magnified observation state.
Figure 3:
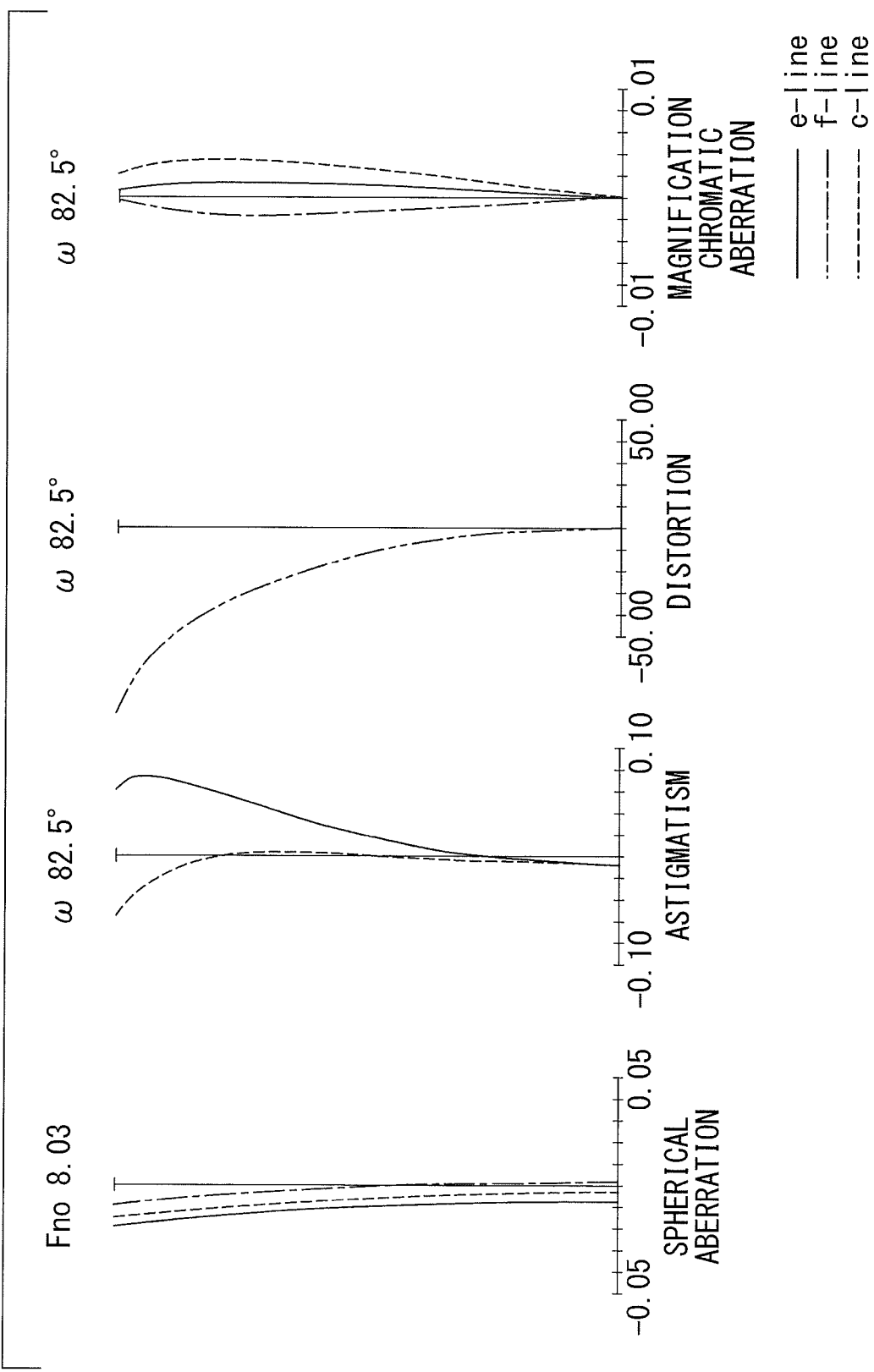
FIG. 3 shows aberration diagrams of the objective optical system in FIG. 2A in the normal observation state.
Figure 4:
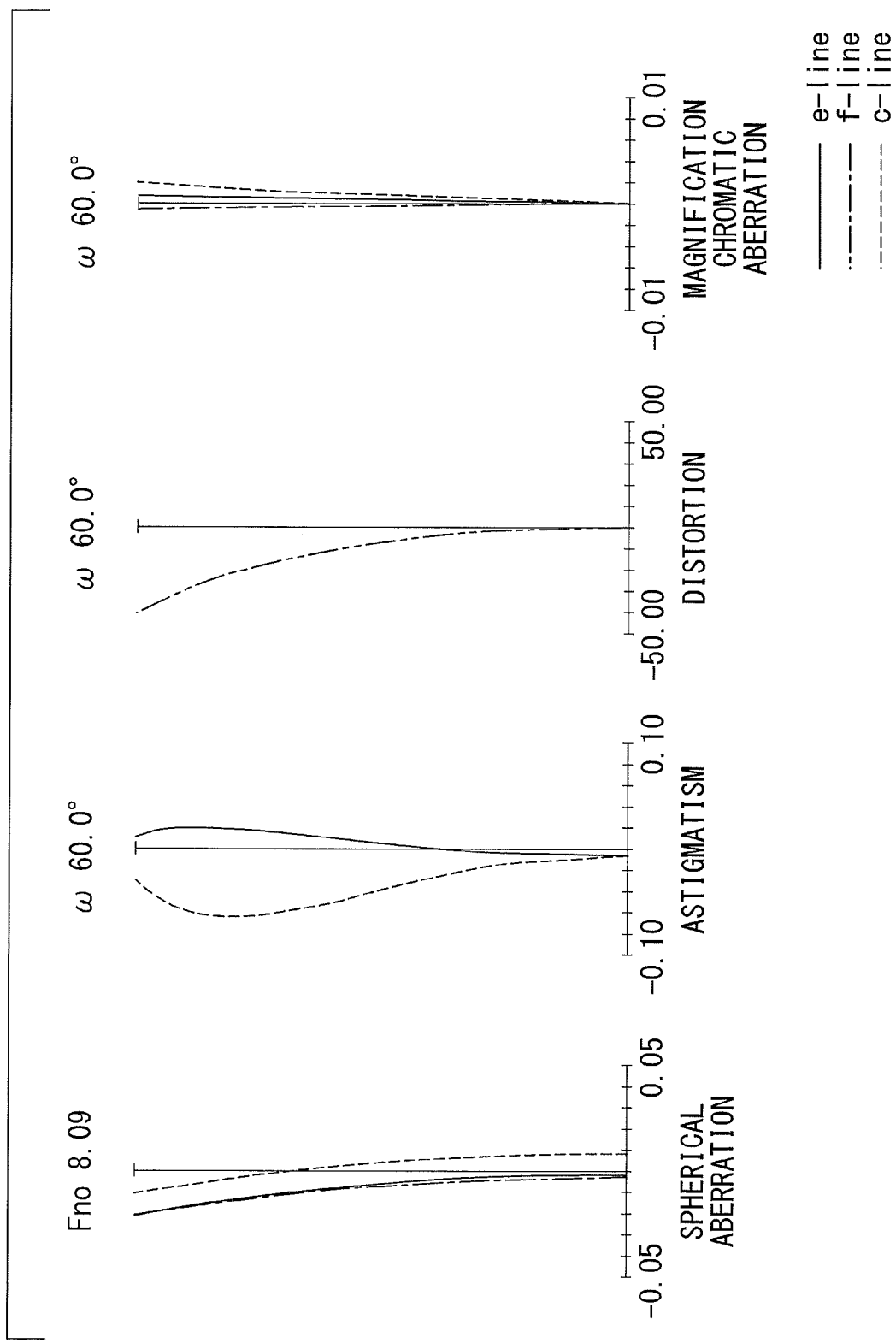
FIG. 4 shows aberration diagrams of the objective optical system in FIG. 2B in the intermediate state.

FIG. 2A, FIG. 2B, and FIG. 2C show the configuration of an objective optical system according to Example 1 of the present invention. FIG. 2A shows a normal observation state, FIG. 2B shows an intermediate state, and FIG. 2C shows a magnified observation state. FIG. 3 shows aberration diagrams of the objective optical system according to this Example in the normal observation state, FIG. 4 shows aberration diagrams in the intermediate state, and FIG. 5 shows aberration diagrams in the magnified observation state.

The lens data for the objective optical system according to Example 1 of the present invention is shown below.

| Lens Data | | | | |
|---|---|---|---|---|
| Surface number | r | d | Ne | Vd |
| 1 | ∞ | 0.38 | 1.88815 | 40.76 |
| 2 | 1.363 | 0.85 | | |
| 3 | ∞ | 0.31 | 1.51564 | 75.00 |
| 4 | ∞ | 1.45 | | |
| 5 | −5.355 | 1.05 | 1.65222 | 33.79 |
| 6 | −2.355 | 0.03 | | |
| 7 | 4.019 | 0.98 | 1.77621 | 49.60 |
| 8 | −3.296 | 0.30 | 1.93429 | 18.90 |
| 9 | −19.843 | D9 | | |
| 10 | Aperture stop | 0.01 | | |
| 11 | ∞ | 0.28 | 1.48915 | 70.23 |
| 12 | 1.455 | 0.38 | 1.59667 | 35.31 |
| 13 | 1.912 | D13 | | |
| 14 | 3.915 | 1.52 | 1.48915 | 70.23 |
| 15 | −3.915 | 0.04 | | |
| 16 | 13.704 | 1.54 | 1.48915 | 70.23 |
| 17 | −2.584 | 0.42 | 1.93429 | 18.90 |
| 18 | −6.244 | 0.52 | | |
| 19 | ∞ | 0.40 | 1.52498 | 59.89 |
| 20 | ∞ | 0.65 | | |
| 21 | ∞ | 0.80 | 1.51825 | 64.14 |
| 22 | ∞ | 0.80 | 1.50801 | 60.00 |
| 23 | Imaging surface | | | |

| Miscellaneous data | Normal observation | Intermediate | Magnified observation |
|---|---|---|---|
| Focal length | 1.70 | 1.8 | 1.85 |
| Fno | 7.09 | 8.09 | 8.15 |
| Object distance | 18.0 | 4.0 | 2.0 |
| D9 | 0.32 | 0.85 | 1.38 |
| D13 | 1.64 | 1.11 | 0.58 |

Example 2

Figure 6A:
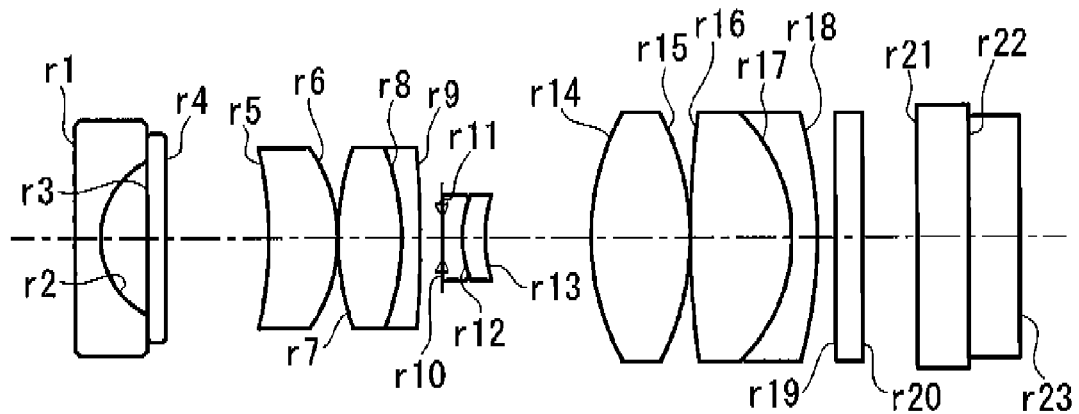
FIG. 6A is a cross-sectional view showing the overall configuration of an objective optical system according to Example 2 of the present invention, and shows a normal observation state.
Figure 6B:
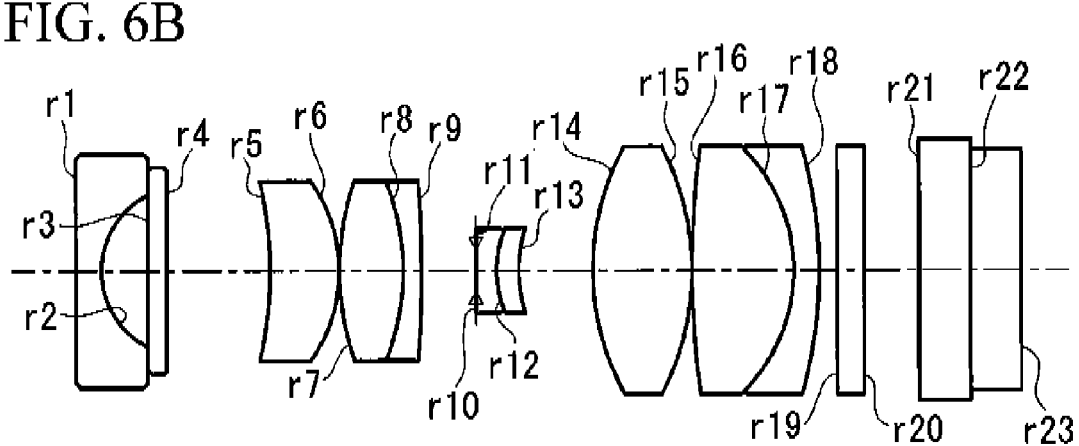
FIG. 6B is a cross-sectional view showing the overall configuration of an objective optical system according to Example 2 of the present invention, and shows an intermediate state.
Figure 6C:
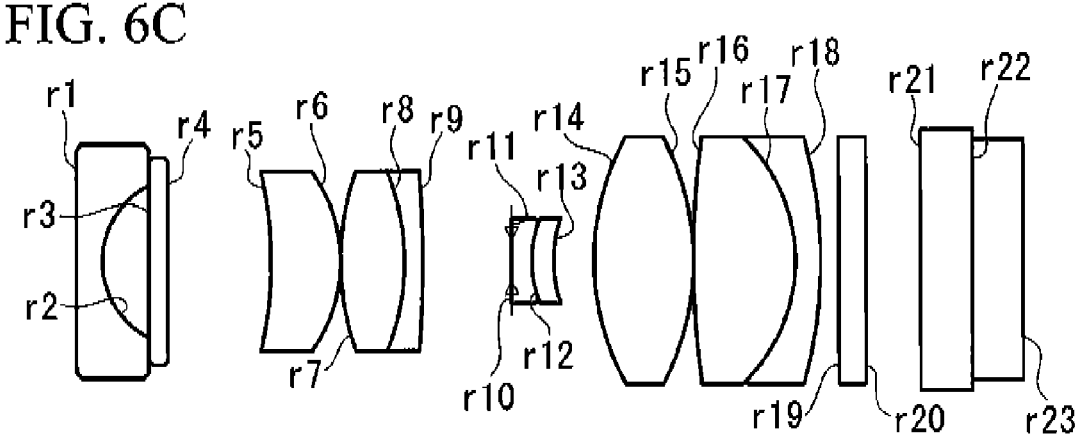
FIG. 6C is a cross-sectional view showing the overall configuration of an objective optical system according to Example 2 of the present invention, and shows a magnified observation state.
Figure 7:
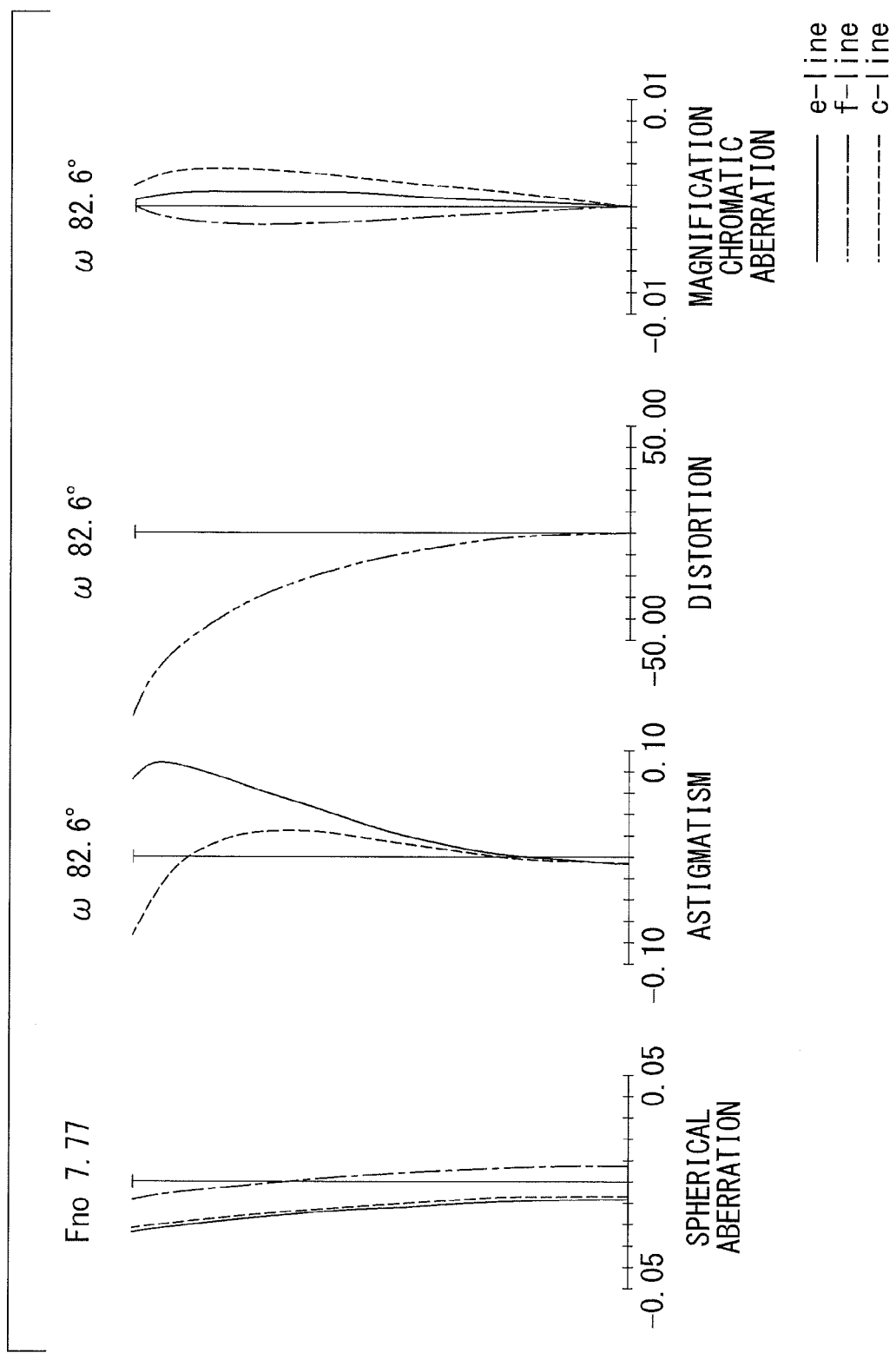
FIG. 7 shows aberration diagrams of the objective optical system in FIG. 6A in the normal observation state.
Figure 8:
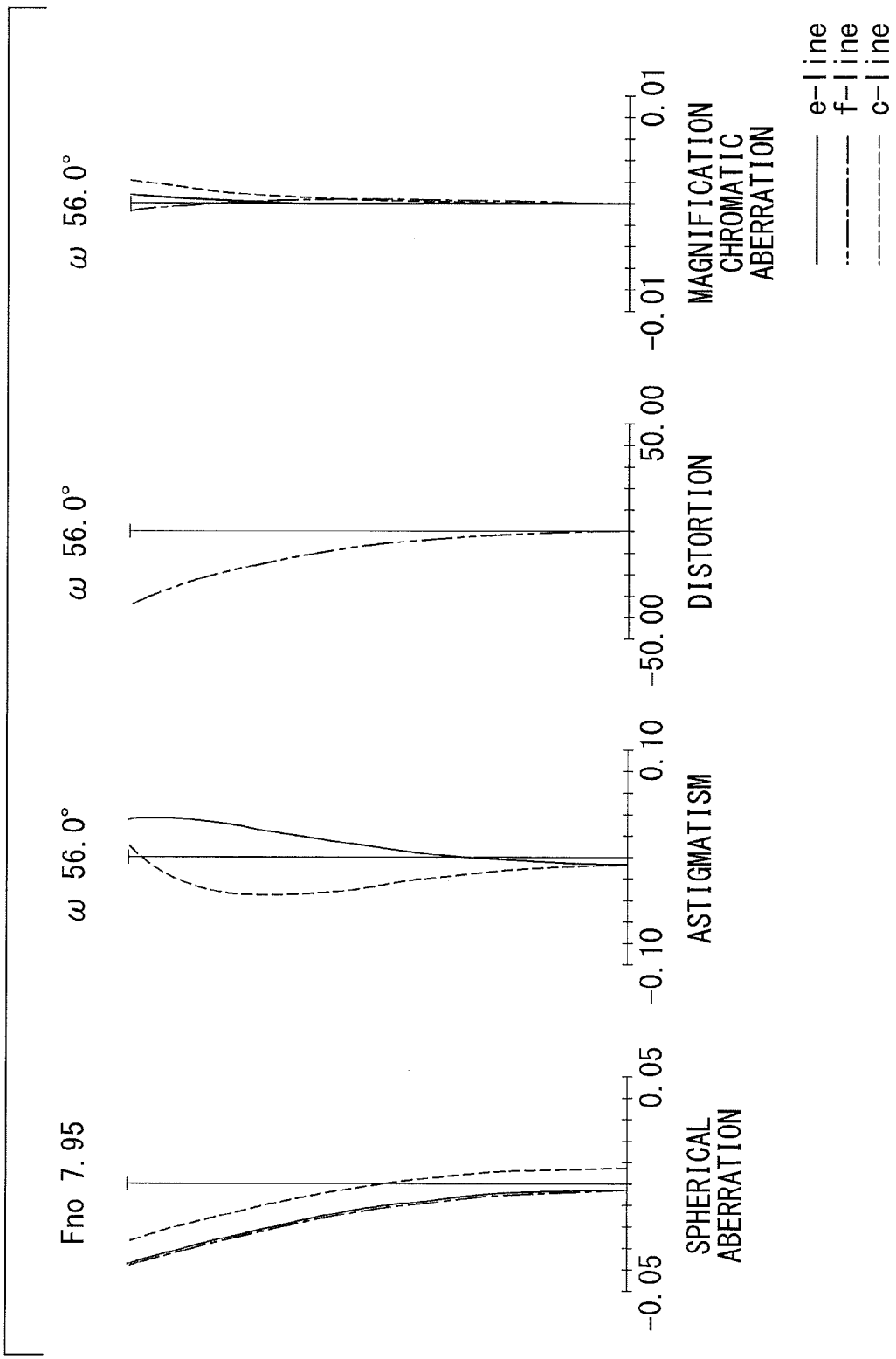
FIG. 8 shows aberration diagrams of the objective optical system in FIG. 6B in the intermediate state.
Figure 9:
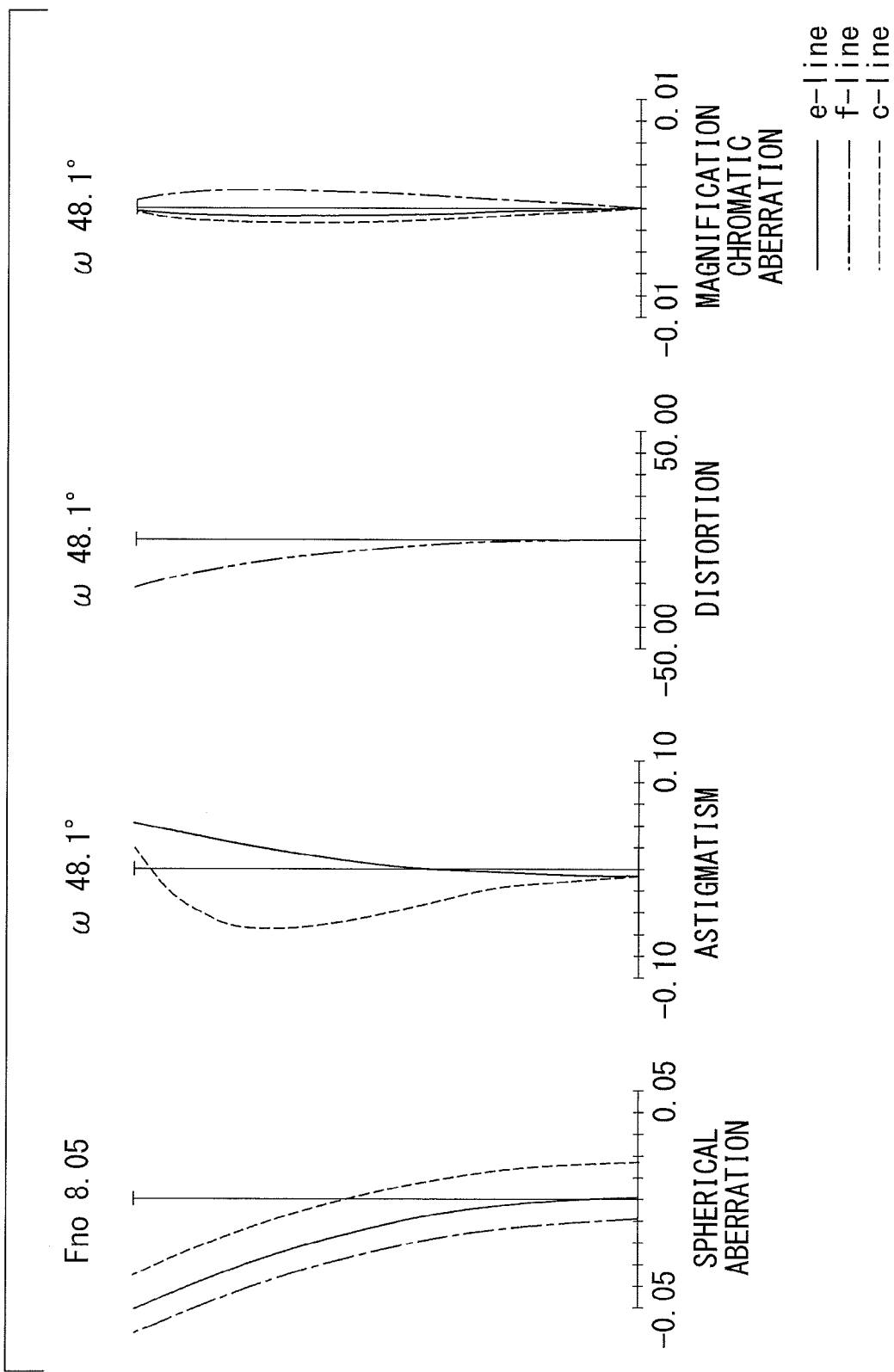
FIG. 9 shows aberration diagrams of the objective optical system in FIG. 6C in the magnified observation state.

FIG. 6A, FIG. 6B, and FIG. 6C show the configuration of an objective optical system according to Example 2 of the present invention. FIG. 6A shows a normal observation state, FIG. 6B shows an intermediate state, and FIG. 6C shows a magnified observation state. FIG. 7 shows aberration diagrams of the objective optical system according to this Example in the normal observation state, FIG. 8 shows aberration diagrams in the intermediate state, and FIG. 9 shows aberration diagrams in the magnified observation state.

The lens data for the objective optical system according to Example 2 of the present invention is shown below.

| Lens Data | | | | |
|---|---|---|---|---|
| Surface number | r | d | Ne | Vd |
| 1 | ∞ | 0.38 | 1.88815 | 40.76 |
| 2 | 1.396 | 0.85 | | |
| 3 | ∞ | 0.31 | 1.51564 | 75.00 |
| 4 | ∞ | 1.45 | | |
| 5 | −4.100 | 1.05 | 1.51977 | 52.43 |
| 6 | −2.255 | 0.03 | | |
| 7 | 3.759 | 0.98 | 1.77621 | 49.60 |
| 8 | −3.759 | 0.30 | 1.93429 | 18.90 |
| 9 | −10.341 | D9 | | |
| 10 | Aperture stop | 0.018 | | |
| 11 | ∞ | 0.274 | 1.48915 | 70.23 |
| 12 | 1.416 | 0.313 | 1.59667 | 35.31 |
| 13 | 1.760 | D13 | | |
| 14 | 3.865 | 1.494 | 1.48915 | 70.23 |
| 15 | −3.865 | 0.039 | | |
| 16 | 6.224 | 1.552 | 1.48915 | 70.23 |
| 17 | −2.944 | 0.411 | 1.93429 | 18.90 |

Example 3

Figure 10A:
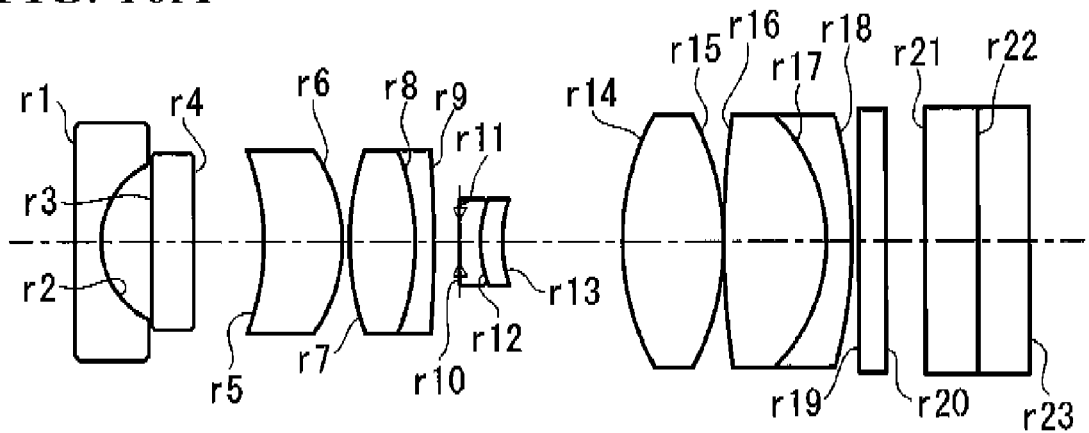
FIG. 10A is a cross-sectional view showing the overall configuration of an objective optical system according to Example 3 of the present invention, and shows a normal observation state.
Figure 10B:
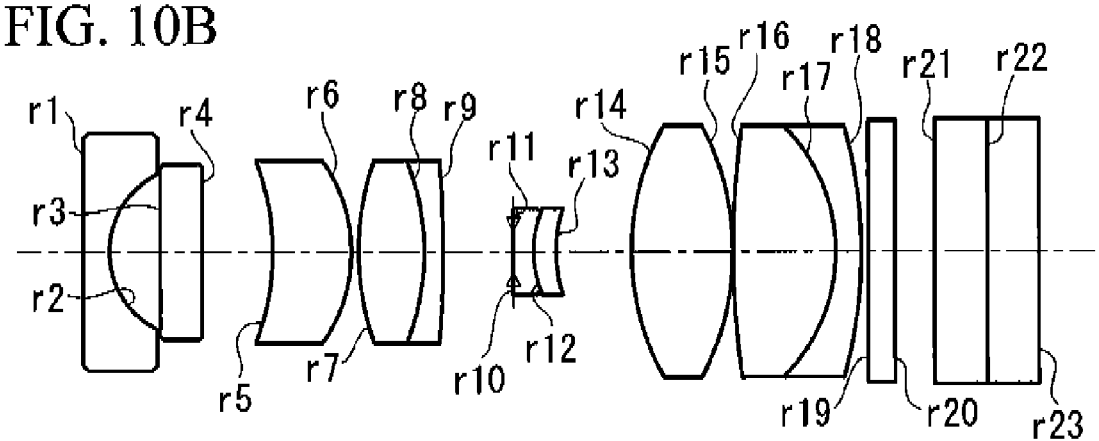
FIG. 10B is a cross-sectional view showing the overall configuration of an objective optical system according to Example 3 of the present invention, and shows an intermediate state.
Figure 10C:
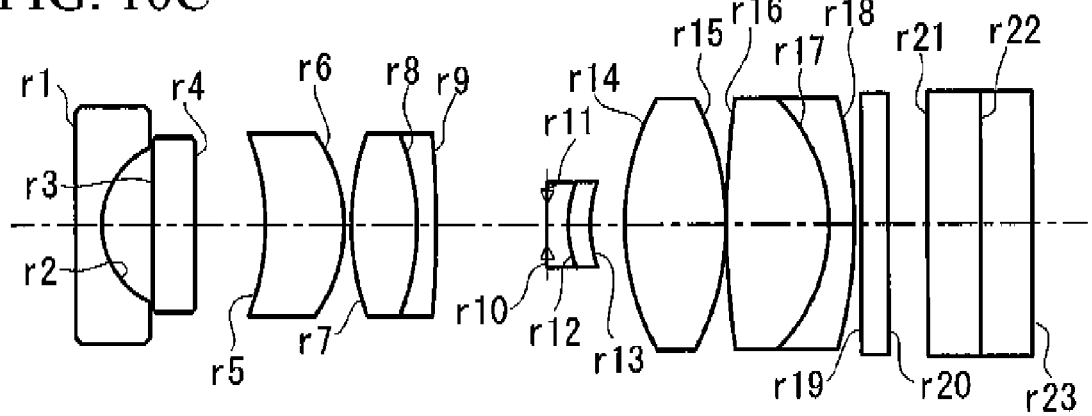
FIG. 10C is a cross-sectional view showing the overall configuration of an objective optical system according to Example 3 of the present invention, and shows a magnified observation state.
Figure 11:
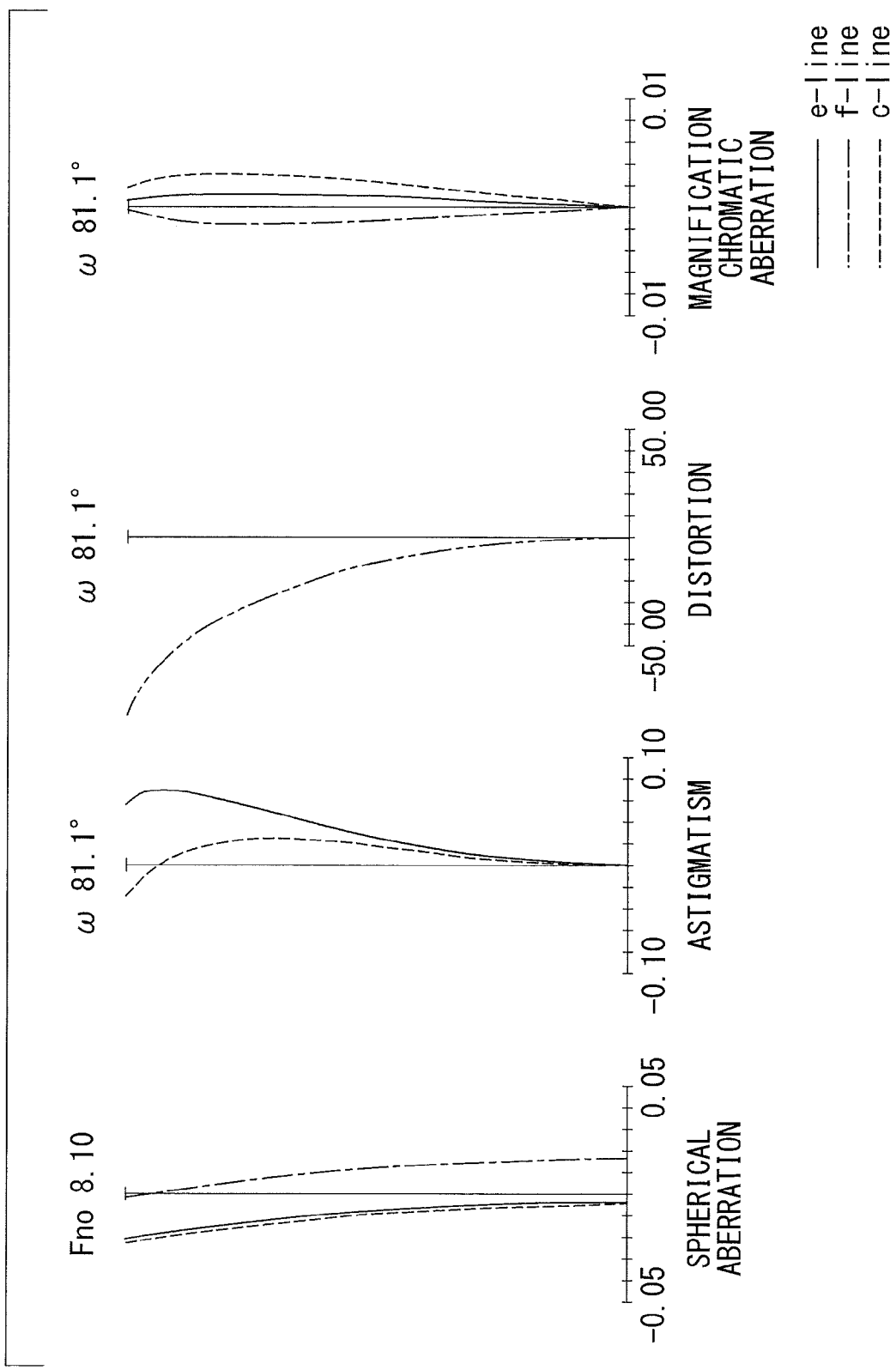
FIG. 11 shows aberration diagrams of the objective optical system in FIG. 10A in the normal observation state.
Figure 12:
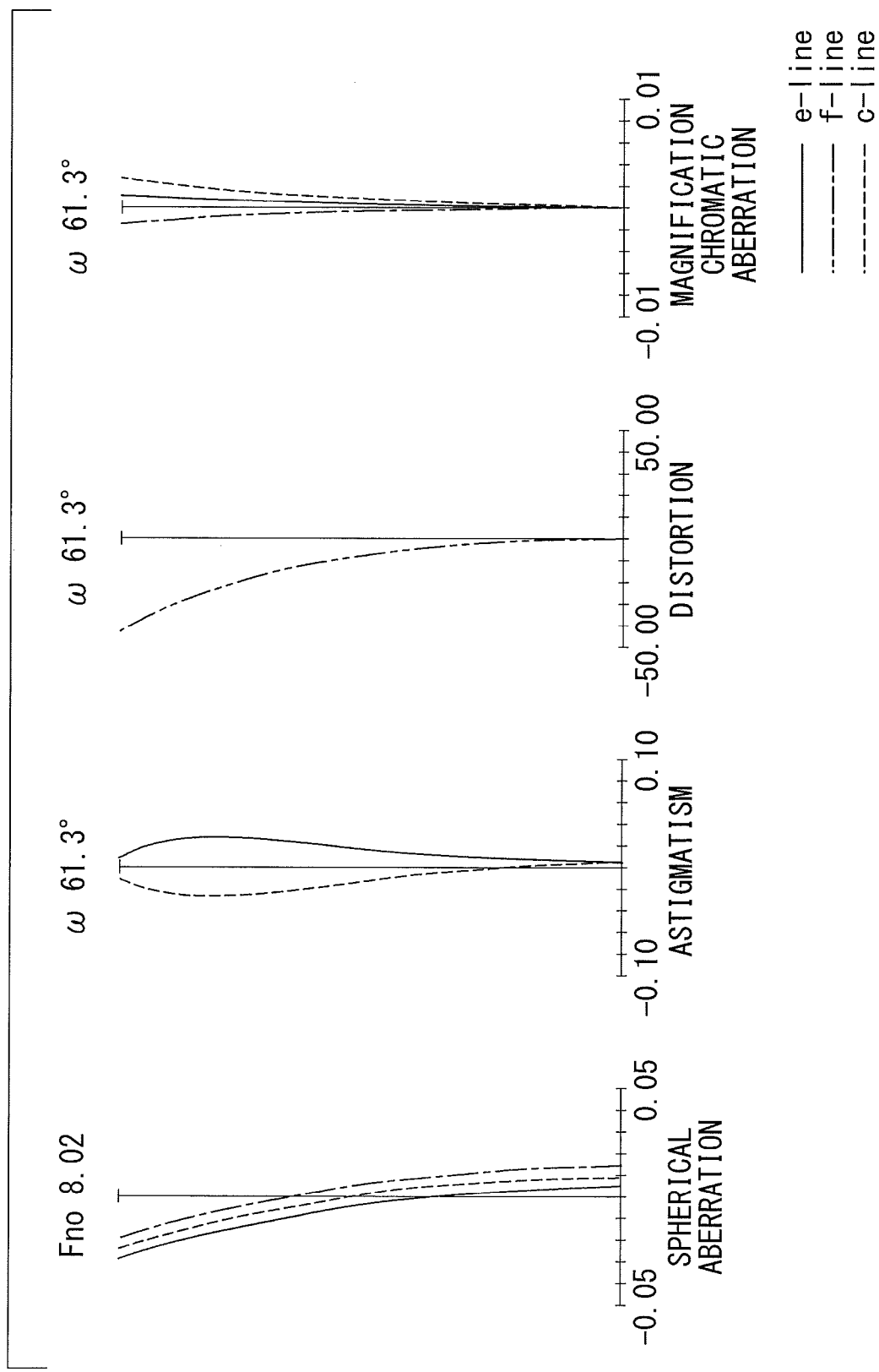
FIG. 12 shows aberration diagrams of the objective optical system in FIG. 10B in the intermediate state.
Figure 13:
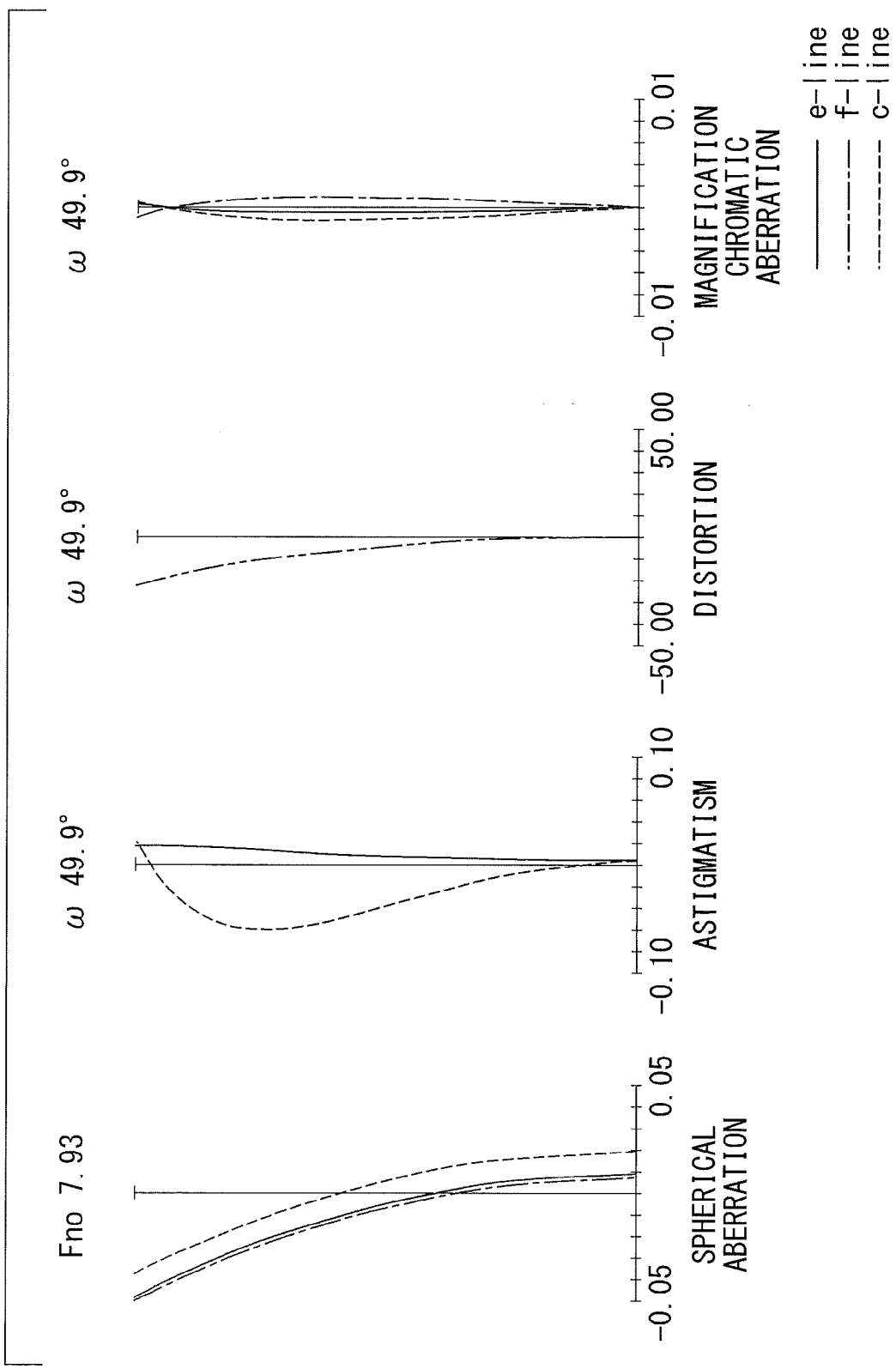
FIG. 13 shows aberration diagrams of the objective optical system in FIG. 10C in the magnified observation state.

FIG. 10A, FIG. 10B, and FIG. 10C show the configuration of an objective optical system according to Example 3 of the present invention. FIG. 10A shows a normal observation state, FIG. 10B shows an intermediate state, and FIG. 10C shows a magnified observation state. FIG. 11 shows aberration diagrams of the objective optical system according to this Example in the normal observation state, FIG. 12 shows aberration diagrams in the intermediate state, and FIG. 13 shows aberration diagrams in the magnified observation state.

The lens data for the objective optical system according to Example 3 of the present invention is shown below.

| Lens Data | | | | |
|---|---|---|---|---|
| Surface number | r | d | Ne | Vd |
| 1 | ∞ | 0.365 | 1.88815 | 40.76 |
| 2 | 1.390 | 0.700 | | |
| 3 | ∞ | 0.600 | 1.51500 | 75.00 |
| 4 | ∞ | 1.034 | | |
| 5 | −2.796 | 1.184 | 1.51977 | 52.43 |
| 6 | −2.277 | 0.029 | | |
| 7 | 3.921 | 1.005 | 1.77621 | 49.60 |
| 8 | −3.259 | 0.275 | 1.93429 | 18.90 |
| 9 | −7.335 | D9 | | |
| 10 | Aperture stop | 0.025 | | |
| 11 | 6.155 | 0.275 | 1.48915 | 70.23 |
| 12 | 1.591 | 0.314 | 1.59667 | 35.31 |
| 13 | 1.726 | D13 | | |
| 14 | 3.395 | 1.431 | 1.49846 | 81.54 |
| 15 | −4.353 | 0.039 | | |
| 16 | 24.398 | 1.569 | 1.48915 | 70.23 |
| 17 | −2.293 | 0.392 | 1.93429 | 18.90 |
| 18 | −6.117 | 0.100 | | |
| 19 | ∞ | 0.400 | 1.52498 | 59.89 |
| 20 | ∞ | 0.600 | | |
| 21 | ∞ | 1.000 | 1.51825 | 64.14 |
| 22 | ∞ | 0.640 | 1.50801 | 60.00 |
| 23 | Imaging surface | | | |

Continued:

| Lens Data | | | | |
|---|---|---|---|---|
| 18 | −13.823 | 0.350 | | |
| 19 | ∞ | 0.390 | 1.52498 | 59.89 |
| 20 | ∞ | 0.906 | | |
| 21 | ∞ | 1.000 | 1.51825 | 64.14 |
| 22 | ∞ | 0.570 | 1.51825 | 64.14 |
| 23 | Imaging surface | | | |

| Miscellaneous data | Normal observation | Intermediate | Magnified observation |
|---|---|---|---|
| Focal length | 1.69 | 1.76 | 1.80 |
| Fno | 7.77 | 8.22 | 8.38 |
| Object distance | 17.6 | 3.3 | 2.05 |
| D9 | 0.313 | 0.664 | 1.027 |
| D13 | 1.592 | 0.968 | 0.605 |

Example 4

Figure 14A:
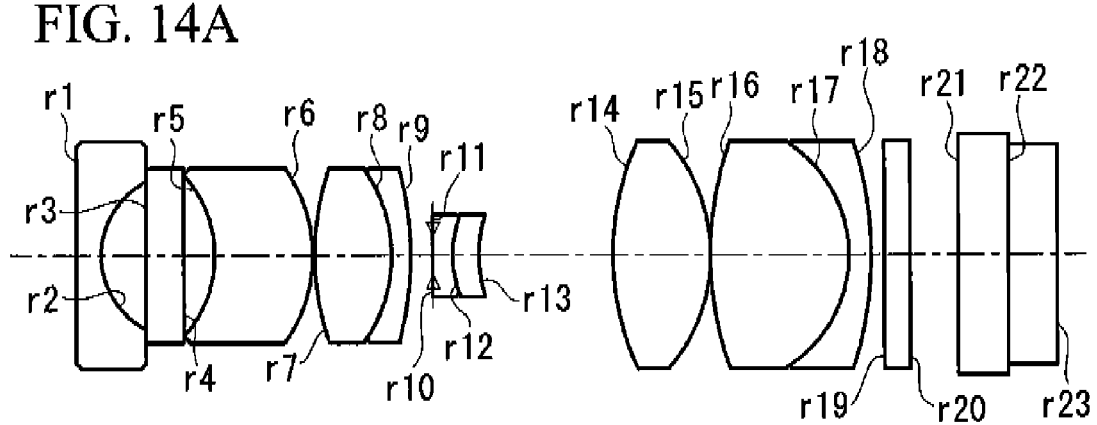
FIG. 14A is a cross-sectional view showing the overall configuration of an objective optical system according to Example 4 of the present invention, and shows a normal observation state.
Figure 14B:
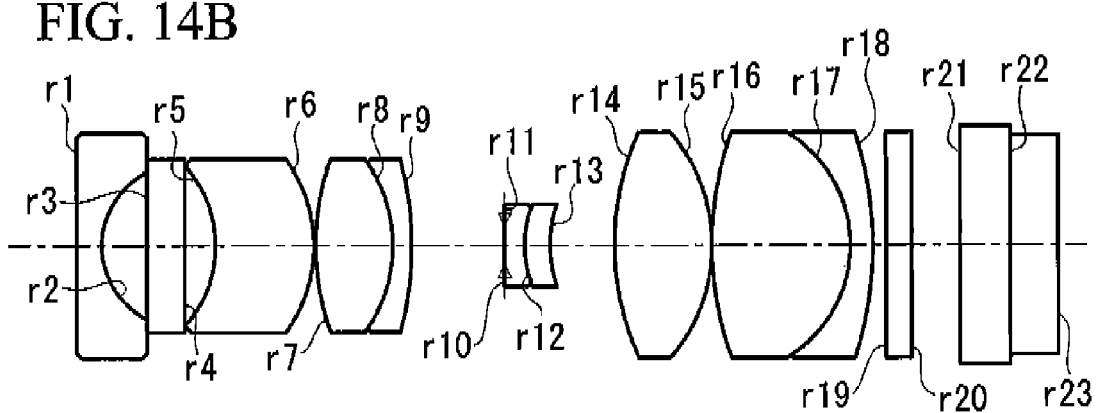
FIG. 14B is a cross-sectional view showing the overall configuration of an objective optical system according to Example 4 of the present invention, and shows an intermediate state.
Figure 14C:
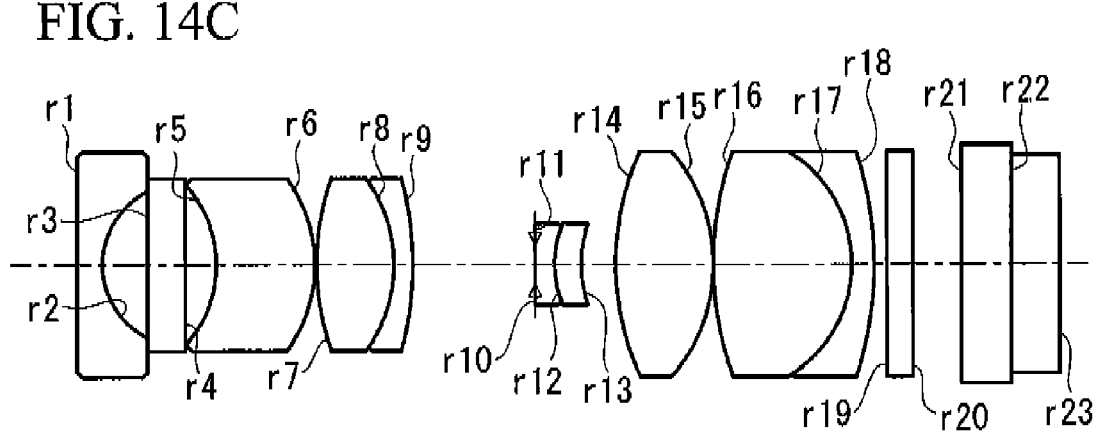
FIG. 14C is a cross-sectional view showing the overall configuration of an objective optical system according to Example 4 of the present invention, and shows a magnified observation state.
Figure 15:
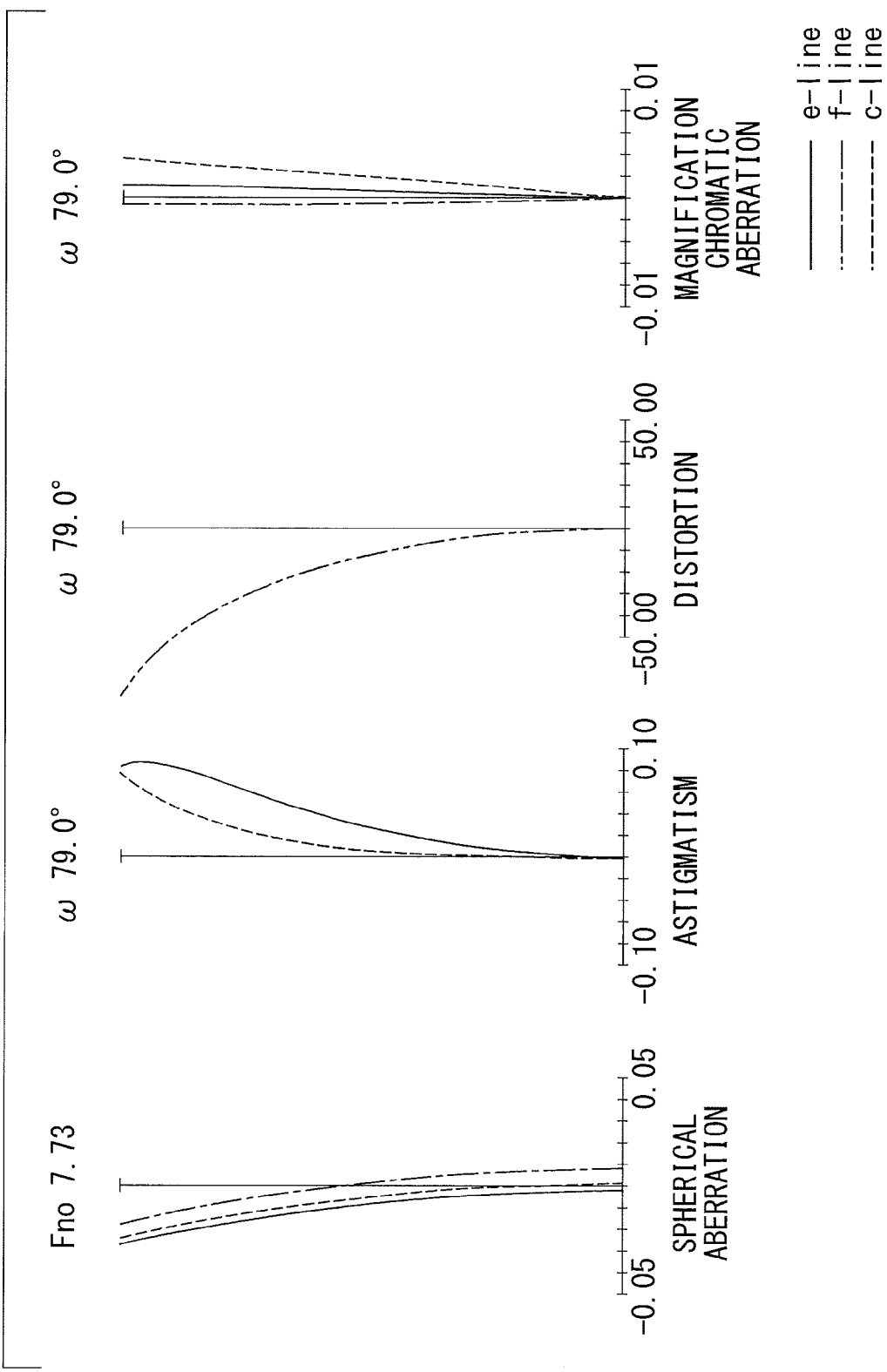
FIG. 15 shows aberration diagrams of the objective optical system in FIG. 14A in the normal observation state.
Figure 16:
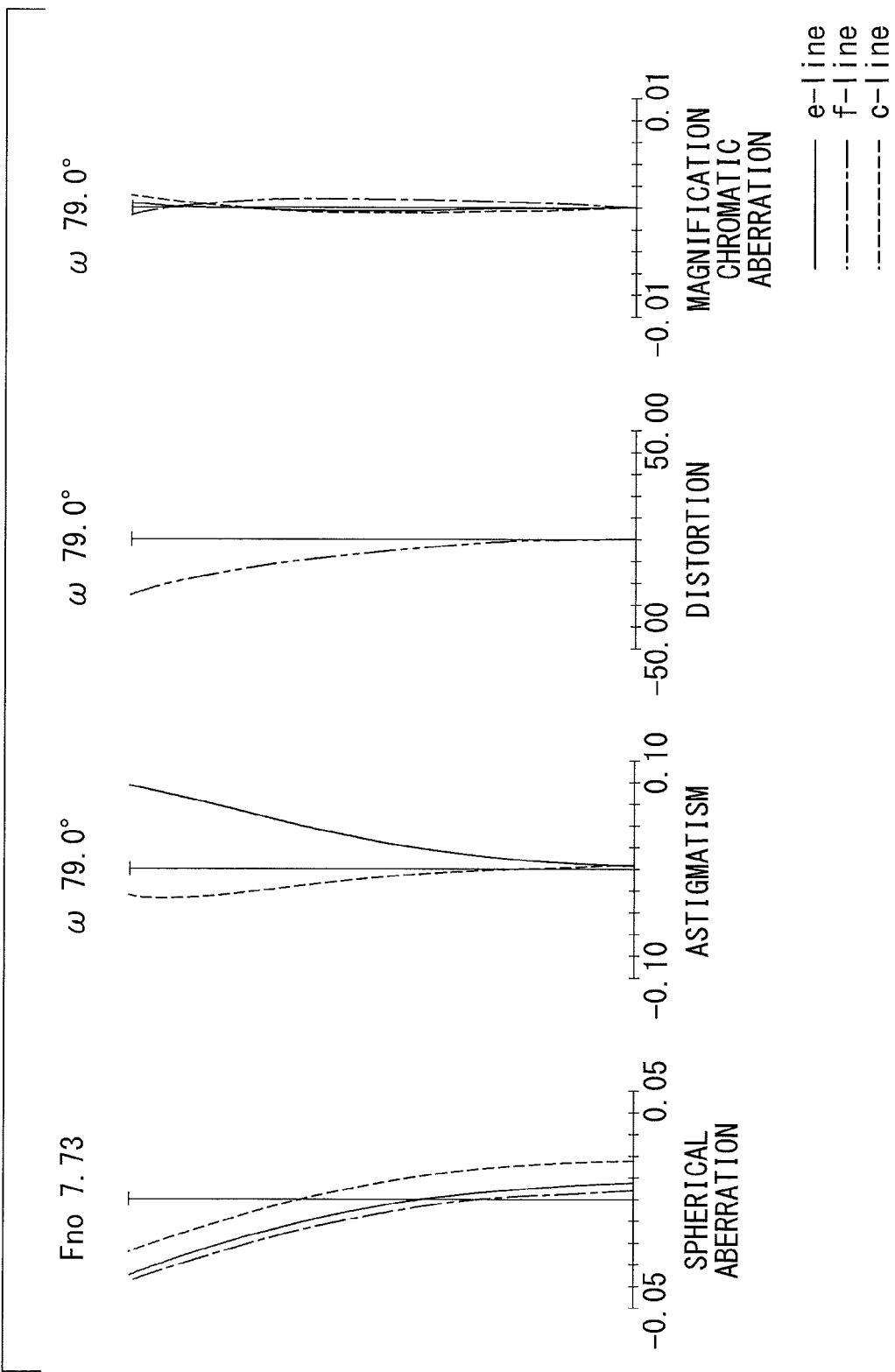
FIG. 16 shows aberration diagrams of the objective optical system in FIG. 14B in the intermediate state.
Figure 17:
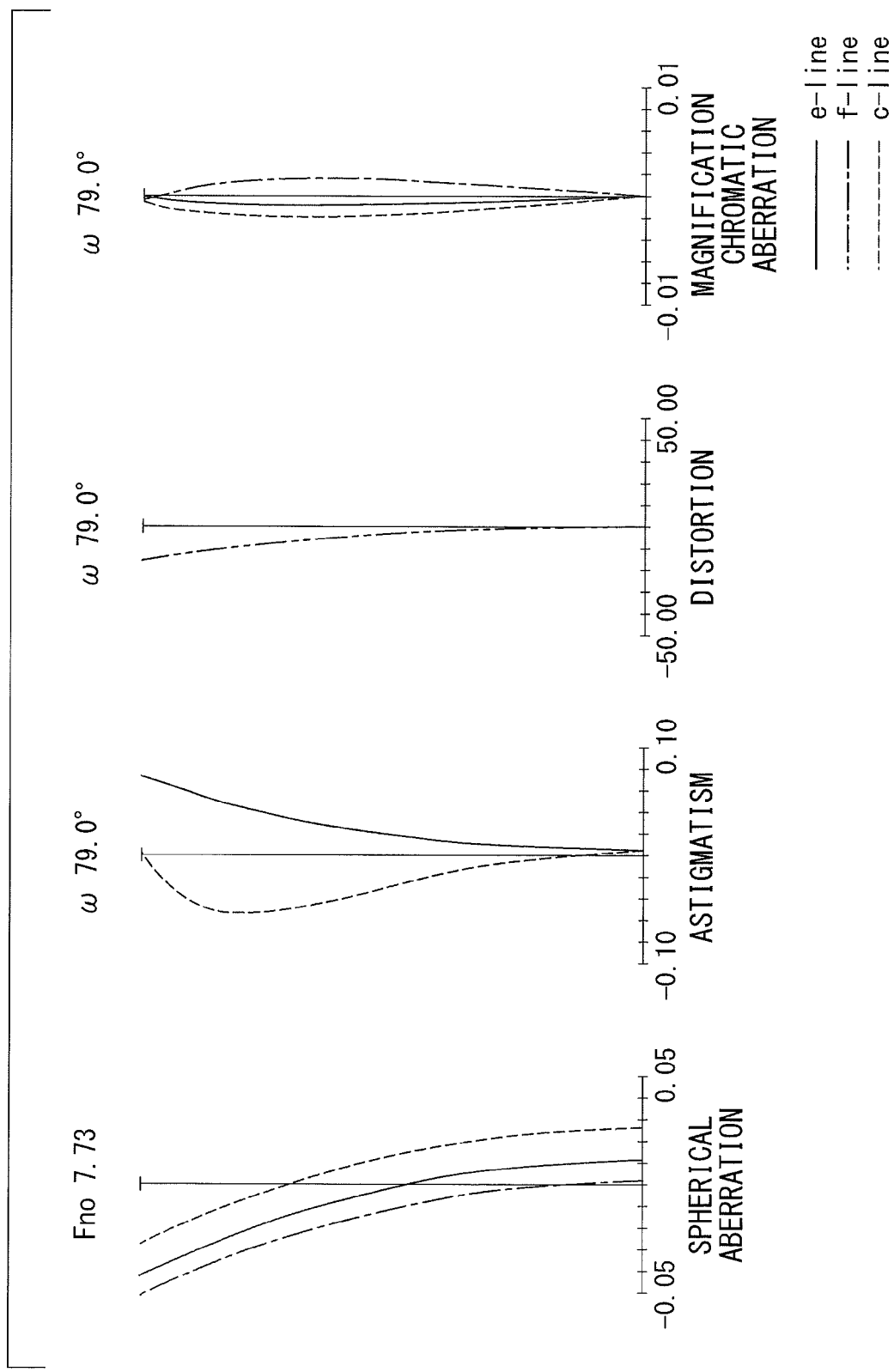
FIG. 17 shows aberration diagrams of the objective optical system in FIG. 14C in the magnified observation state.

FIG. 14A, FIG. 14B, and FIG. 14C show the configuration of an objective optical system according to Example 4 of the present invention. FIG. 14A shows a normal observation state, FIG. 14B shows an intermediate state, and FIG. 14C shows a magnified observation state. FIG. 15 shows aberration diagrams of the objective optical system according to this Example in the normal observation state, FIG. 16 shows aberration diagrams in the intermediate state, and FIG. 17 shows aberration diagrams in the magnified observation state.

The lens data for the objective optical system according to Example 4 of the present invention is shown below.

| Lens Data | | | | |
|---|---|---|---|---|
| Surface number | r | d | Ne | Vd |
| 1 | ∞ | 0.41 | 1.88815 | 40.76 |
| 2 | 1.580 | 0.66 | | |
| 3 | ∞ | 0.60 | 1.52300 | 65.13 |
| 4 | ∞ | 0.52 | | |
| 5 | −2.435 | 1.59 | 1.75453 | 35.33 |
| 6 | −2.838 | 0.03 | | |
| 7 | 5.064 | 1.21 | 1.77621 | 49.60 |
| 8 | −2.767 | 0.30 | 1.93429 | 18.90 |
| 9 | −5.358 | D9 | | |
| 10 | Aperture stop | 0.03 | | |
| 11 | ∞ | 0.32 | 1.48315 | 70.23 |
| 12 | 1.838 | 0.43 | 1.59667 | 35.31 |
| 13 | 2.355 | D13 | | |
| 14 | 5.580 | 1.51 | 1.48915 | 70.23 |
| 15 | −3.509 | 0.04 | | |
| 16 | 6.733 | 2.26 | 1.48915 | 70.23 |
| 17 | −2.436 | 0.36 | 1.93429 | 18.90 |
| 18 | −7.411 | 0.18 | | |
| 19 | ∞ | 0.40 | 1.52510 | 58.50 |
| 20 | ∞ | 0.75 | | |
| 21 | ∞ | 1.00 | 1.51825 | 64.14 |
| 22 | ∞ | 0.64 | 1.51825 | 64.14 |
| 23 | Imaging surface | | | |

| Miscellaneous data | Normal observation | Intermediate | Magnified observation |
|---|---|---|---|
| Focal length | 1.66 | 1.90 | 1.96 |
| Fno | 7.73 | 8.01 | 8.13 |
| Object distance | 16.3 | 3.45 | 2.48 |
| D9 | 0.33 | 1.46 | 1.94 |
| D13 | 2.13 | 1.00 | 0.52 |

Example 5

Figure 18A:
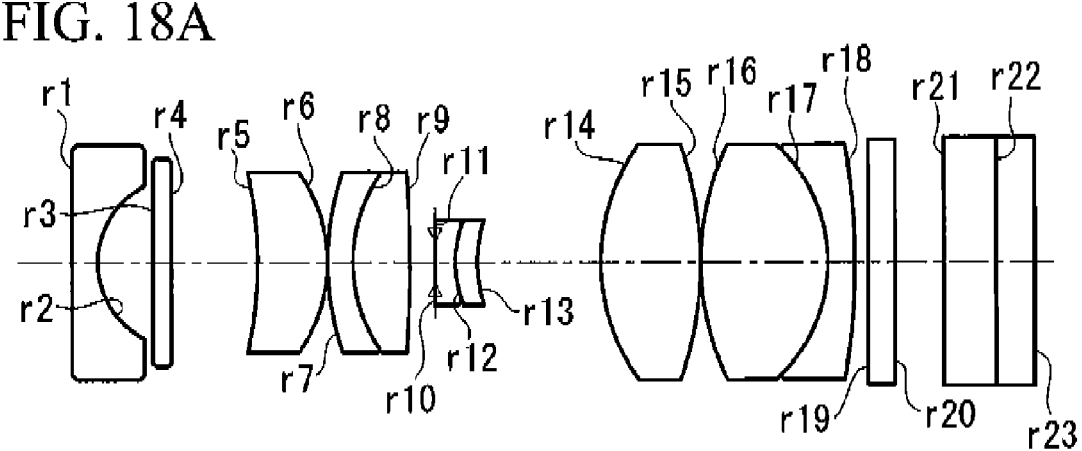
FIG. 18A is a cross-sectional view showing the overall configuration of an objective optical system according to Example 5 of the present invention, and shows a normal observation state.
Figure 18B:
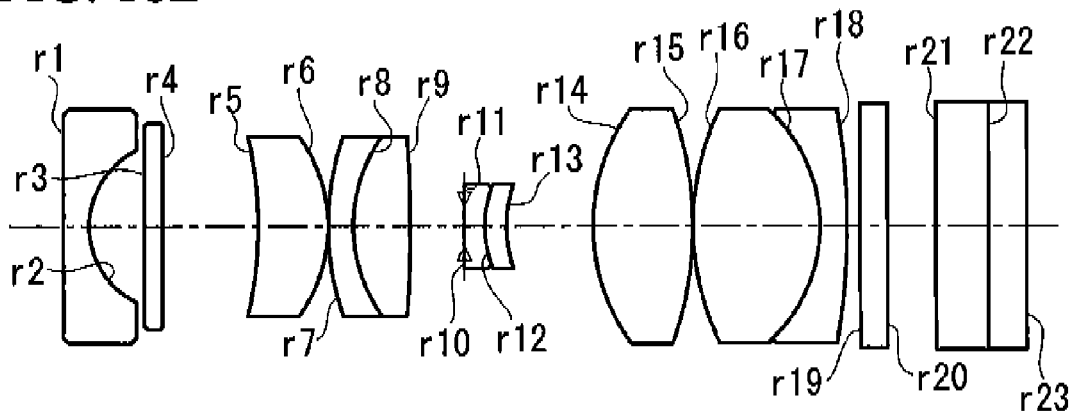
FIG. 18B is a cross-sectional view showing the overall configuration of an objective optical system according to Example 5 of the present invention, and shows an intermediate state.
Figure 18C:
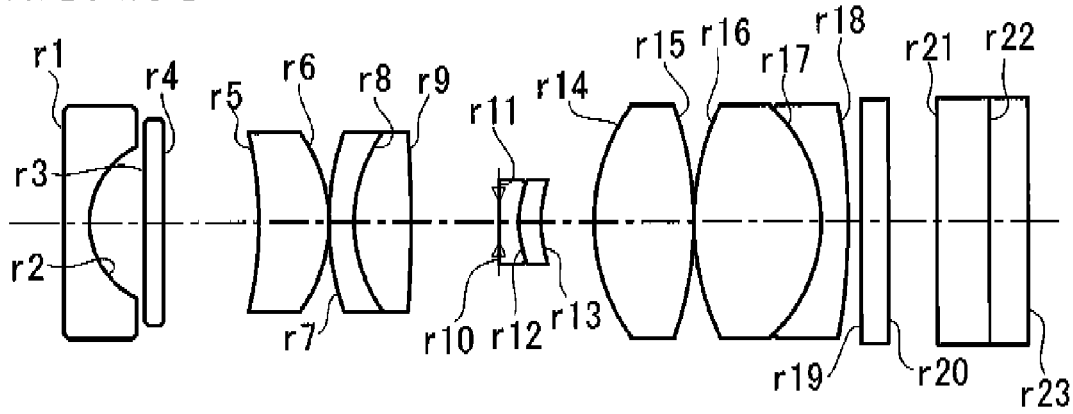
FIG. 18C is a cross-sectional view showing the overall configuration of an objective optical system according to Example 5 of the present invention, and shows a magnified observation state.
Figure 19:
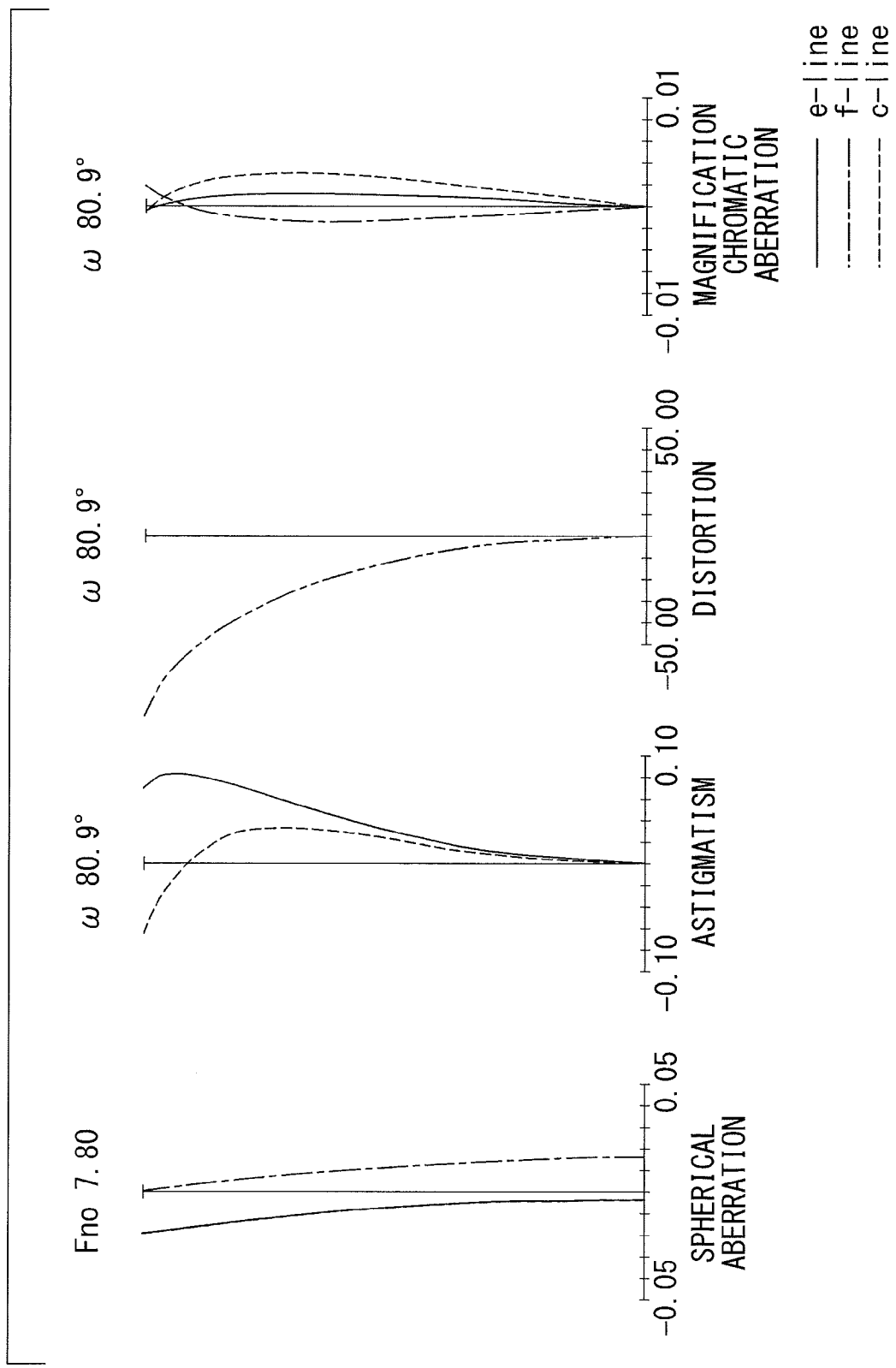
FIG. 19 shows aberration diagrams of the objective optical system in FIG. 18A in the normal observation state.
Figure 20:
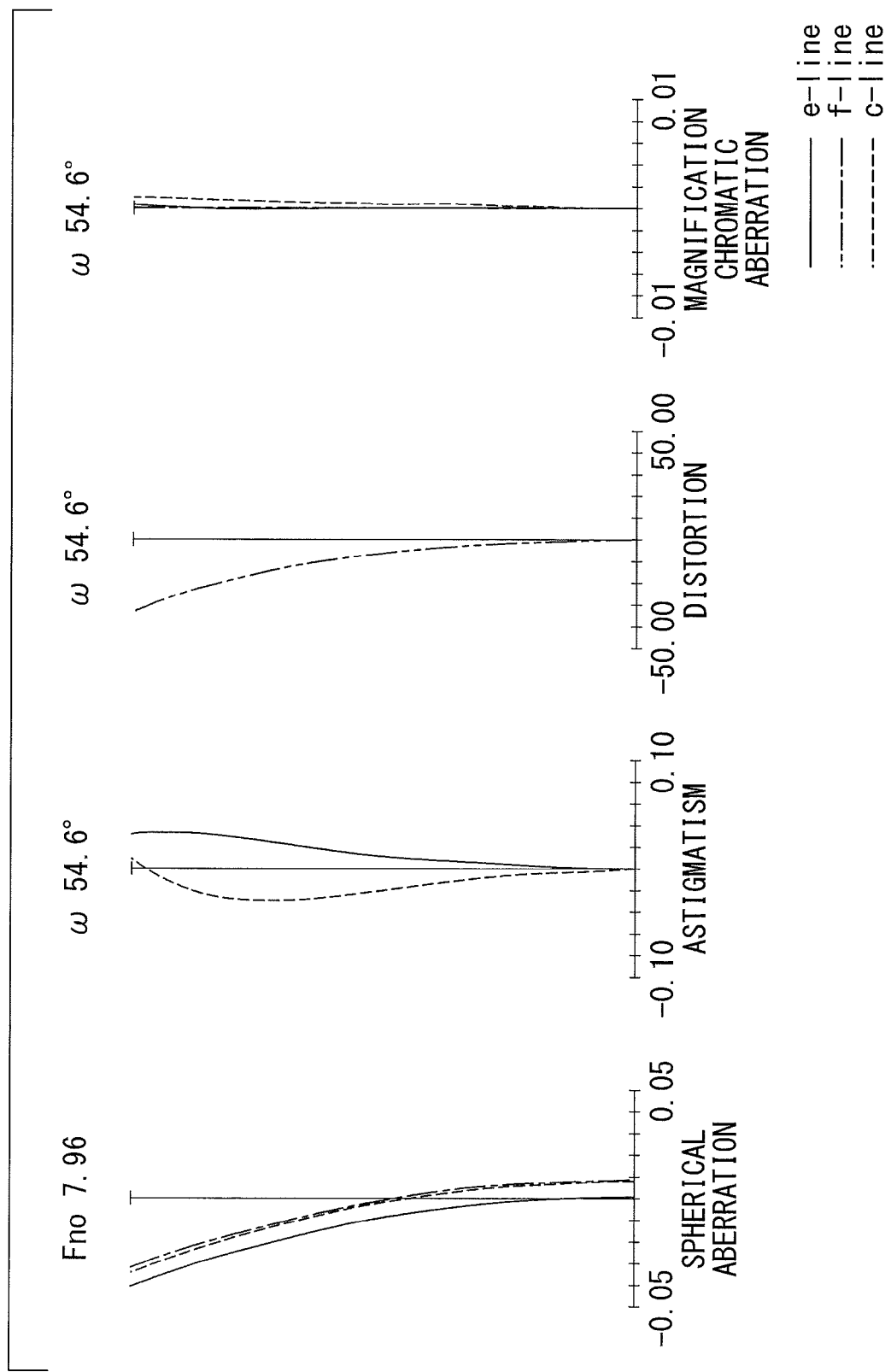
FIG. 20 shows aberration diagrams of the objective optical system in FIG. 18B in the intermediate state.
Figure 21:
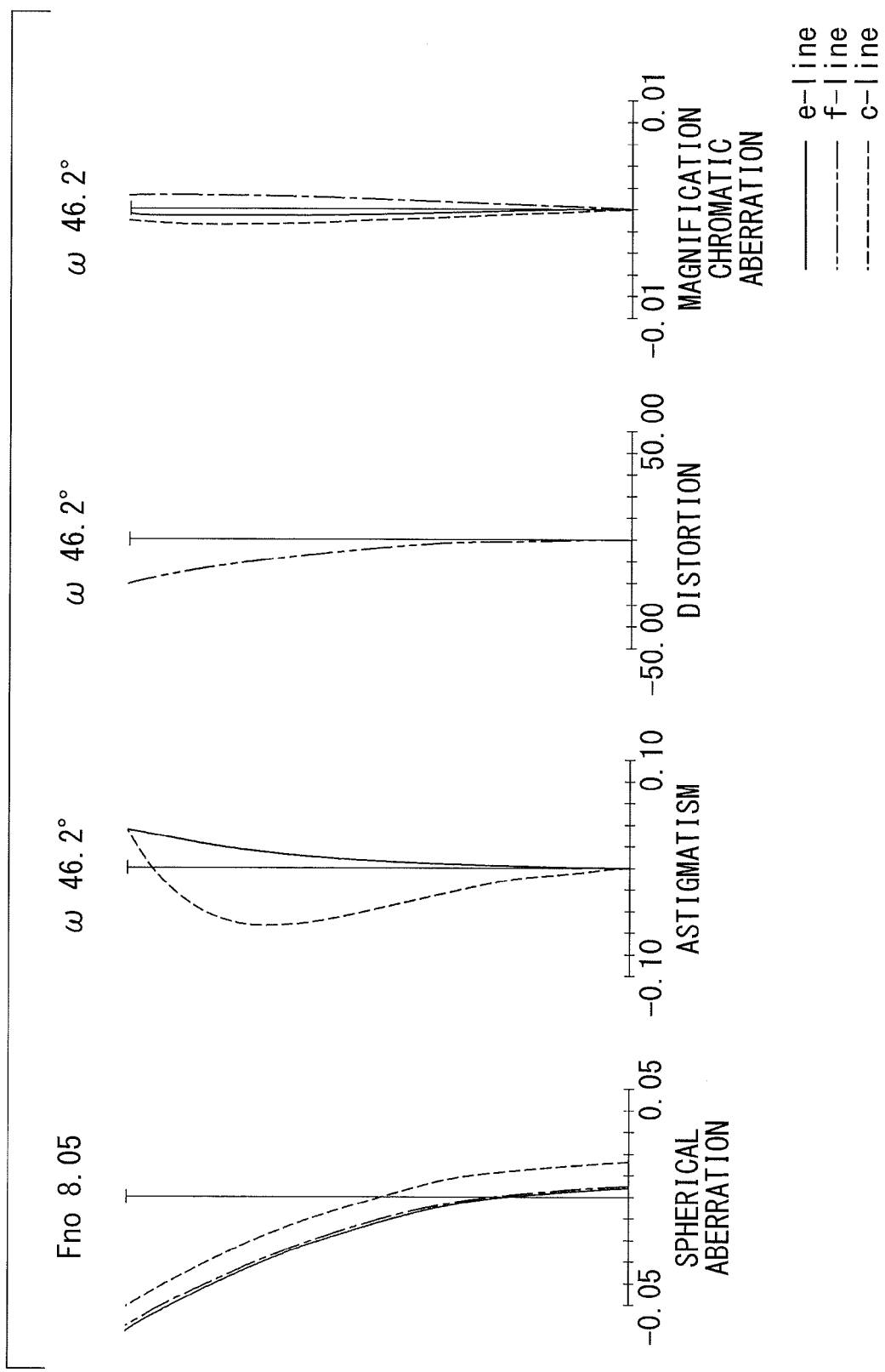
FIG. 21 shows aberration diagrams of the objective optical system in FIG. 18C in the magnified observation state.

FIG. 18A, FIG. 18B, and FIG. 18C show the configuration of an objective optical system according to Example 5 of the present invention. FIG. 18A shows a normal observation state, FIG. 18B shows an intermediate state, and FIG. 18C shows a magnified observation state. FIG. 19 shows aberration diagrams of the objective optical system according to this Example in the normal observation state, FIG. 20 shows aberration diagrams in the intermediate state, and FIG. 21 shows aberration diagrams in the magnified observation state.

The lens data for the objective optical system according to Example 5 of the present invention is shown below.

Lens Data

| Surface number | r | d | Ne | Vd |
|---|---|---|---|---|
| 1 | ∞ | 0.37 | 1.88815 | 40.76 |
| 2 | 1.467 | 0.82 | | |
| 3 | ∞ | 0.30 | 1.51564 | 75.00 |
| 4 | ∞ | 1.31 | | |
| 5 | −3.430 | 1.04 | 1.51977 | 52.43 |
| 6 | −2.400 | 0.03 | | |
| 7 | 3.245 | 0.31 | 1.93429 | 18.90 |
| 8 | 1.955 | 0.91 | 1.77621 | 49.60 |
| 9 | −11.174 | D9 | | |
| 10 | Aperture stop | 0.02 | | |
| 11 | ∞ | 0.27 | 1.48915 | 70.23 |
| 12 | 1.366 | 0.31 | 1.59667 | 35.31 |
| 13 | 1.822 | D13 | | |
| 14 | 3.363 | 1.42 | 1.48915 | 70.23 |
| 15 | −6.411 | 0.04 | | |
| 16 | 4.644 | 1.94 | 1.48915 | 70.23 |
| 17 | −2.484 | 0.41 | 1.93429 | 18.90 |
| 18 | −10.757 | 0.20 | | |
| 19 | ∞ | 0.38 | 1.52498 | 59.89 |
| 20 | ∞ | 0.74 | | |
| 21 | ∞ | 0.80 | 1.51825 | 64.14 |
| 22 | ∞ | 0.60 | 1.51825 | 64.14 |
| 23 | Imaging surface | | | |

| Miscellaneous data | Normal observation | Intermediate | Magnified observation |
|---|---|---|---|
| Focal length | 1.71 | 1.84 | 1.87 |
| Fno | 7.80 | 7.96 | 8.05 |
| Object distance | 17.4 | 3.28 | 2.02 |
| D9 | 0.31 | 1.01 | 1.43 |
| D13 | 1.95 | 1.25 | 0.83 |

Table 1 shows the values of conditional expressions (1) to (13) in the configurations of Examples 1 to 5 above.

TABLE 1

| Conditional expression | Example 1 | Example 2 | Example 3 | Example 4 | Example 5 |
|---|---|---|---|---|---|
| (1) | −3.69 | −5.13 | −8.47 | −18.34 | −6.92 |
| (2) | 0.62 | 0.59 | 0.78 | 0.97 | 0.66 |
| (3) | 1.07 | 1.05 | 1.18 | 1.43 | 1.09 |
| (4) | −2.53 | −2.3 | −3.37 | −3.15 | −2.4 |
| (5) | 2.39 | 2.32 | 2.66 | 2.42 | 2.3 |
| (6) | 1.06 | 0.99 | 1.27 | 1.3 | 1.04 |
| (7) | 0.42 | 0.45 | 0.35 | 0.45 | 0.45 |
| (8) | 82.51 | 82.6 | 81.08 | 79.04 | 80.93 |
| (9) | 48.69 | 48.09 | 49.9 | 45.3 | 46.21 |
| (10) | 1.22 | 1.23 | 1.25 | 1.58 | 1.22 |
| (11) | 0.58 | 0.57 | 0.55 | 0.6 | 0.57 |
| (12) | 0.79 | 0.79 | 0.79 | 0.78 | 0.79 |
| (13) | 0.79 | 0.8 | 0.81 | 0.82 | 0.81 |

Additional Items

An objective optical system according to claim 1 or claim 2 in which any of the following conditional expressions are satisfied:

$$0.95 < g1/f < 1.65 \quad (3)$$

$$-4 < g2/f < -2 \quad (4)$$

$$2.1 < g3/f < 2.9 \quad (5)$$

$$0.7 < |g2/g3| < 1.5 \quad (6)$$

$$0.3 < |g1/g2| < 0.5 \quad (7)$$

$$w1 > 75 \quad (8)$$

$$w2 < 55 \quad (9)$$

$$1.0 < ltl/f/(\beta2/\beta1) < 1.8 \quad (10)$$

$$0.4 < IH/p/1000 < 0.7 \quad (11)$$

$$0.5 < h2/h1 < 1.2 \quad (12)$$

$$0.5 < Enp/f < 1.5 \quad (13)$$

Here, g1 is a focal length of the first lens group, g2 is a focal length of the second lens group, and g3 is a focal length of the third lens group.

w1 is a half viewing angle during normal observation, and w2 is a half viewing angle during magnified observation.

ltl is a total length of the optical system (a distance from the object-side surface of the first lens to the imaging surface), β1 is a magnification factor at the best object distance in the normal observation state, and β2 is a magnification factor at the best object distance in the magnified observation state.

IH is a maximum image height, p is a pixel pitch, h2 is a maximum ray height at the final surface during magnified observation, h1 is a maximum ray height at the final surface during normal observation, and Enp is an entrance pupil position during normal observation.

REFERENCE SIGNS LIST

G1 first lens group
G2 second lens group
G3 third lens group
L1 first lens
L2 second lens
L3 third lens
L4 fourth lens
L5 fifth lens
L6 sixth lens
L7 seventh lens
L8 eighth lens
L9 ninth lens
CL1 combined lens
CL2 combined lens
CL3 combined lens
S aperture stop
F1 parallel flat plate
F2 parallel flat plate
CG cover glass

The invention claimed is:

1. An objective optical system consists of, in order from an object side to an image side: a first lens group having positive optical power; a second lens group having negative optical power; and a third lens group having positive optical power, wherein the first lens group includes, in order from the object side to the image side, a first lens having negative optical power and a second lens having positive optical power, and the second lens group is moved according to a change in an object distance to perform focusing, and conditional expressions below are satisfied:

$-19 < f2/f1 \leq -3.69$ $0.5 < v/f < 1.1$ $0.3 < |g1/g2| < 0.5$ where f2 is a focal length of the second lens, and f1 is a focal length of the first lens;

v is an amount of movement of the second lens group, and f is a focal length of an entire system during a most distant view observation; and g1 is a focal length of the first lens group, g2 is a focal length of the second lens group.

2. The objective optical system according to claim 1, wherein the second lens is a positive meniscus lens in which the object side is a concave surface.

* * * * *